(12) United States Patent
Adams

(10) Patent No.: US 8,152,526 B2
(45) Date of Patent: Apr. 10, 2012

(54) DENTAL IMPLANT

(75) Inventor: Curtis Adams, Flemington, NJ (US)

(73) Assignee: CH Scientific, LLC, Flemington, NJ (US)

( * ) Notice: Subject to any disclaimer, the term of this patent is extended or adjusted under 35 U.S.C. 154(b) by 712 days.

(21) Appl. No.: 11/943,926

(22) Filed: Nov. 21, 2007

(65) Prior Publication Data
US 2008/0124675 A1    May 29, 2008

Related U.S. Application Data

(63) Continuation-in-part of application No. 11/603,749, filed on Nov. 22, 2006, now abandoned.

(51) Int. Cl.
*A61C 8/00* (2006.01)
(52) U.S. Cl. ....................................... 433/174
(58) Field of Classification Search .......... 433/172–176, 433/201.1, 202.1, 215, 220, 221; 606/280, 606/70, 286, 300, 301
See application file for complete search history.

(56) References Cited

U.S. PATENT DOCUMENTS

| | | | |
|---|---|---|---|
| 4,086,701 A | 5/1978 | Kawahara et al. |
| 4,438,183 A | 3/1984 | Baughman et al. |
| 4,516,937 A | 5/1985 | Bosker |
| 5,082,445 A | 1/1992 | Singer |
| 5,118,295 A | 6/1992 | Stiles |
| 5,120,222 A | 6/1992 | Sulc |
| 5,195,891 A | 3/1993 | Sulc |
| 5,342,199 A | 8/1994 | Gillespie |
| 5,513,989 A | 5/1996 | Crisio |
| 5,564,925 A | 10/1996 | Shampanier |
| 5,749,732 A | 5/1998 | Sendax |
| 5,839,899 A | 11/1998 | Robinson |
| 5,989,030 A | 11/1999 | Suga |
| 6,250,924 B1 | 6/2001 | Luotio |
| 6,319,000 B1 | 11/2001 | Br.ang.nemark |
| 6,537,069 B1 | 3/2003 | Simmons, Jr. |
| 6,632,088 B2 | 10/2003 | Voudouris |
| 6,663,387 B2 * | 12/2003 | Riley ............................ 433/173 |
| 6,695,616 B2 | 2/2004 | Ellison |
| 6,716,030 B1 | 4/2004 | Bulard et al. |

(Continued)

FOREIGN PATENT DOCUMENTS
WO    WO 2004/064664    8/2004

(Continued)

OTHER PUBLICATIONS

Imtec Corporation, "Long-Term Denture Stabilization," 2004 (3 pages).

(Continued)

*Primary Examiner* — Cris L Rodriguez
*Assistant Examiner* — Heidi M Eide
(74) *Attorney, Agent, or Firm* — Frommer Lawrence & Haug LLP

(57) ABSTRACT

Dental implants for fixed and removable prosthetic devices, and for other devices such as orthodontic devices, which have application to single tooth replacement, e.g., caps and crowns, and multiple tooth replacement using one or more implants, e.g., bridges, and multiple implants for full and partial prosthetic devices. The dental implants include a post or posts inserted into the jawbone and a base that is loaded, in the general area of the gum line, against the jawbone using the post or posts. The base may be loaded against the jawbone by a fastener system.

21 Claims, 15 Drawing Sheets

U.S. PATENT DOCUMENTS

| | | |
|---|---|---|
| 6,793,491 B2 | 9/2004 | Klein et al. |
| 7,108,511 B1 | 9/2006 | Shatkin |
| 2005/0084822 A1 | 4/2005 | Stucki-McCormick |
| 2005/0100864 A1 | 5/2005 | Elian |
| 2006/0154204 A1 | 7/2006 | Reggie |
| 2008/0118885 A1 | 5/2008 | Devincenzo et al. |

FOREIGN PATENT DOCUMENTS

| | | |
|---|---|---|
| WO | WO 2005/016168 | 2/2005 |
| WO | WO 2006/038209 | 4/2006 |
| WO | WO 2006/082610 | 8/2006 |
| WO | WO 2009/029718 | 3/2009 |

OTHER PUBLICATIONS

Nobel Biocare, "NobelDirect 3.0 Clinical Procedure & Product Catalog," Catalog 2004 (pp. 4-7).

510(K) No. K031106, "Imtech Sendax MDI and Mdi Plus Endosseous Implant, Models OB-XX, SH-XX, MOB-22, MSH-XX", dated Aug. 12, 2003, 4 pgs.

510(K) No. K972351, "Sendax MDI (Mini Dental Implant)", dated Nov. 24, 1997, 5 pgs.

510(K) No. K023067, "Imtec Sendax MDI ORTHO6 and OTHO8", dated Dec. 3, 2002, 2 pgs.

510(K) No. K990983, "Modification to Imtec Sendax MDI", dated Apr. 13, 1999, 5 pgs.

510(K) No. K070601, "Mini Drive-Lock Dental Implant System", dated Oct. 12, 2007, 6 pgs.

"Imtec MDI Sendax Long-Term Denture Stabilization" http://www.imtec.com/demo/mdi_product.php, download date Apr. 7, 2010, 2 pgs.

"Sendax MDI Mini Dental Implant System" http://www.dentalcompare.com/showcase.asp?showcaseid=225, download date Apr. 7, 2010, 2 pgs.

"Imtec Sendax MDI System" http://www.imtec.com/implants/products_MDI.php, download date Apr .7, 2010, 1pg, including color catalog copyright dated 2009, 29 pgs.

"How to Profit from the MDI System" http://waybackmachine.org/web/20050311020204/http://imtec.com:80/demo/profit_from_mdi.php, download dated Apr. 7, 2010, 3 pgs.

"Increased Treatment Solution—Intra Lock International Inc." http://intra-lock.com/index.php?option=com_contact&task=view&id=36&Itemid=72, download date Apr. 7, 2010, 1 pg.

Theories and Techniques of Oral Implantology, Leonard I. Linkow, vol. One, pp. 23, Fig. 5-17, Fig. 5-66, The CV Mosby Company, St. Louis, 1970.

Bicon, "Bicon Dentl Implants," Website available at http://bicon.com/patent/dental_implants.html (c) 2004 (2 pages).

Imtec, "The Imtec MDI System Instructions for Use," Product nstructions (2 pages), at least as early as Nov. 21, 2006. Admitted to be prior art.

* cited by examiner

DENTAL IMPLANT

This application is a continuation-in-part of application Ser. No. 11/603,749 filed on Nov. 22, 2006 now abandoned. The priority of application Ser. No. 11/603,749 is hereby claimed under 35 U.S.C. §120.

BACKGROUND OF THE INVENTION

The invention disclosed herein relates generally to dental implants for fixed and removable prosthetic devices and to fixed and removable prosthetic devices including such implants, and for other devices such as orthodontic devices, for example.

Implant dentistry dates back at least to the 1970s. See, e.g., *Principles and Practice of Implant Dentistry*, by Charles M. Weiss and Adam Weiss, Mosby Inc., 2001.

SUMMARY OF THE INVENTION

The invention provides dental implants for fixed and removable prosthetic devices, and for other applications such as orthodontics, and to fixed and removable prosthetic devices including such implants, and has application to, but is not limited to, one or more of the following: single tooth replacement, e.g., caps and crowns; multiple tooth replacement using one or more implants, e.g., bridges; and multiple implants for full and partial prosthetic devices. Embodiments of dental implants incorporating the invention may be installed in single or multiple root teeth locations.

Dental implants according to embodiments of the invention comprise a post or posts inserted into the jawbone extending therefrom towards the opposing jawbone, and a base or stabilizer that is loaded, in the general area of the gum line, against the jawbone. Preferably, the base or stabilizer is loaded against the jawbone directly, but in some embodiments may be loaded against the jawbone indirectly, e.g., through gum tissue. Implants, including the post(s) and the base or stabilizer, are intended to be permanent, according to the embodiments of the invention. The base or stabilizer is part of such a permanent implant and hence is also intended to be permanent, as part of the implant. So as not to confuse the base or stabilizer with an endodontic procedure, or a temporary stabilizer for prior art implantology procedures, the base or stabilizer is referred to below simply as a "base," which may comprise a base plate or platform or other structure.

The term loaded or loadable against the jawbone is meant in a broad sense and encompasses loading of the base against the jawbone in direct contact therewith or, in some embodiments, through gum tissue. According to some embodiments, the base is loaded against the jawbone by a force or forces derived from anchoring of the post or posts in the jawbone. For example, the base may be urged in compression against the jawbone via a tensile force applied to the post or posts. According to some embodiments, loading the base against the jawbone also loads the post or posts in tension with respect to the jawbone.

Implants according to the embodiments of the invention incorporating such bases provide sufficient supporting surface area for a prosthetic device even though the size of the post(s) is relatively small, e.g., typically smaller than that of a post previously used for an implant at a particular implant location. A base loaded against the jawbone according to embodiments of the invention allows the use of a post or posts of smaller diameter and yet the base and smaller post(s) cooperate to provide support for a prosthetic (or other) device of the same size as previously used at a particular implant location. Implants, according to embodiments of the invention, comprise one or more of such smaller posts, the size of which depends upon tooth or implant location (incisor, canine, etc.,) and patient characteristics. The combination of a base and a plurality of smaller posts, or a base and a single smaller post, provides improved support for a prosthetic device (or other device) of the same size used previously at a particular tooth or implant location. The base loaded against the jawbone provides improved support and resistance to a load presented by a prosthetic device (or other device) attached to the implant, and improves distribution of the load. The force with which the base is loaded against the jawbone is sufficient to provide such support and resistance.

Also, loading the base against the jawbone promotes bone growth and improves or provides for bonding of the base to the jawbone.

According to some embodiments, the base is configured to fit snugly between existing teeth into the implant location at the gum line, so as to be loadable against the jawbone. For example, the base is configured to fit in a space or cavity at the concerned implant location in the mouth, e.g., in a space between teeth, created by the absence of a tooth, or otherwise, loaded against the jawbone at the gum line. The term tooth location is meant in a broad sense and corresponds at least generally to the location of a tooth formerly in the mouth. For example, the implant may be centered more or less in the location formerly occupied by a tooth, although the implant location may be offset from the center of the location of a tooth formerly in the mouth, e.g., where the space or cavity formerly occupied by the tooth is large or the implant is to be inserted where two or more adjacent teeth were formerly in the mouth. Where there is a large toothless area in the mouth, the implant location need not correspond to that where a tooth was formerly located, but may depend upon patient characteristics. In some embodiments, an implant with an attached prosthetic device is approximately the size of a tooth, but in some embodiments can be larger or smaller depending upon patient characteristics.

Various configurations of bases may be used. According to some embodiments of the invention, the configuration corresponds generally to a cross-sectional slice of the tooth formerly at the tooth location, e.g., such that the base occupies a substantial surface area, e.g., all or most of the surface area, formerly occupied by the tooth at the gum line at the implant location. According to some embodiments of the invention, the base is configured to be received within the width of the jawbone (e.g., the transverse dimension of the jawbone) at the implant location. In some embodiments, the width of the base is approximately the width of or approximately not wider than the width of the jawbone (e.g., the base may be slightly larger than the jawbone) at the implant location. In some embodiments of the invention, the cross-sectional surface area of the base is approximately that of the space or cavity in the implant location at the gum line, i.e., the cross-sectional surface area of the tooth formerly at the implant location at the gum line. According to some embodiments, the length of the base (e.g., the dimension extending along the jawbone) corresponds generally to that of a tooth formerly at the tooth location, but may be longer depending upon patient characteristics.

According to some embodiments of the invention, the thickness of the base is sufficient to withstand the compressive force(s) that load the base against the jawbone and to stabilize a prosthetic device or other device attached to the implant. Also, according to some embodiments of the invention, the prosthesis or other device extends over the base, which should have sufficient thickness to permit this.

In some applications of the invention, an implant or implants may be used to attach a device in the mouth other than a prosthetic device, for example a device used in orthodontics. Depending upon the application, an implant may be inserted into the jawbone in any location suitable for the application. For example, an implant used to anchor an orthodontic device may not be inserted into the jawbone at a location occupied or formerly occupied by a tooth. Those of skill in the art can determine suitable locations for such implants.

In some embodiments of the invention, a fastener system operates to provide or assist in providing loading of the base and/or post or posts. Examples of fastener systems comprise systems which operate to attach or engage the post or posts and the base before, during or after insertion of the post or posts into the jawbone.

In embodiments in which the post(s) and the base are engaged or attached after insertion of the post(s) into the jawbone, the post(s) are inserted into the jawbone and operation of a fastener system attaches or engages the base and the inserted post(s), directly or through engagement of the base with the jawbone, and loads the base and/or post(s).

In embodiments in which the post(s) and the base are attached or engaged during insertion of the post(s) into the jawbone, operation of a fastener system attaches or engages the base and the post(s) during insertion of the post(s), directly or indirectly through engagement of the base with the jawbone, and the base and/or post(s) are loaded during insertion of the post(s) into the jawbone.

In embodiments in which the post(s) and the base are attached or engaged before insertion of the post(s) into the jawbone, the base and the post(s) may form a unitary piece or be attached or engaged together in any suitable manner to form a unit (e.g., by a fastener system), or they may be otherwise engaged (e.g., by a fastener system). The attached or engaged base and post(s), and engagement of the base with the jawbone resulting from insertion of the post(s), function to load the base against the jawbone and/or the post(s) when the post(s) are inserted into the jawbone.

In some embodiments, the base includes a hole for each post, and a respective post is received in a respective hole. In some embodiments, a respective post passes through a respective hole.

In some embodiments, the post or posts comprise screw threads by means of which the post or posts can be secured to the jawbone. In various embodiments, the threaded post(s) may be attached to or engage the base before, during or after insertion of the post(s), as described above. However, in embodiments in which a threaded post and base are attached or engaged prior to insertion, depending upon the manner of insertion, it may not be practical to employ more than one post.

A dental implant according to some embodiments of the invention comprises: at least one post which is inserted into a patient's jawbone extending towards the opposing jawbone; and a base including a hole in a side of the base for each post of the dental implant. According to some embodiments, the relative sizes of each post and the base are such that a transverse or width dimension of the base is substantially larger than a largest transverse dimension, e.g., a diameter, of any of the posts at the location at which the particular post is received in a hole in the base. Each hole and a portion of a corresponding post which in use would be received in a hole may comprise complementary configurations. The configuration of a respective hole and the configuration of a respective post preferably provides but does not have to provide a snug fit. The implant also includes a fastener system as described herein.

Any suitable post and any suitable insertion methodology may be used. For example, in the illustrated embodiments, each post includes a screw thread extending along at least the portion of the post which is to be threaded into the jawbone. In some embodiments, the threaded portion is circular in cross section, and the post diameter may be tapered. In these embodiments in which a post includes screw threads for inserting the post, each such post is secured to the jawbone at least using the screw thread thereof with an end of the respective post extending from the jawbone attached to or engaged with the base.

In some embodiments of the invention, self-tapping posts with screw threads are employed. In some embodiments, a guide hole in the jawbone may be drilled, and the post screwed into the guide hole in a self-tapping manner. In some embodiments, a self-tapping post is screwed directly into the jawbone without a guide hole.

In some embodiments, the base comprises a platform or base plate that includes opposed parallel major sides and at least one minor side transverse to the major sides, e.g., may have a generally solid rectangular, trapezoidal or other suitable configuration. The platform may be rectangular or trapezoidal in cross section, or may have other suitable cross-sectional shapes, e.g., circular, oval, triangular. In some embodiments of the base that comprise at least one hole, in the installed condition of the implant, the at least one post is received in the at least one hole, and in some embodiments passes through the at least one hole with the free end of the post extending beyond an adjacent major side of the platform. A fastener system operates to engage or attach each post and the base, as described herein.

In some embodiments, a base receives a core to which, at least partially, a prosthetic device or other device is attached. In embodiments in which a post and/or fastener system part projects from the base, the core may be used to cover the post and/or fastener part, and at least assist in securing a prosthetic device to the base.

In some embodiments, the core comprises material that is applied to the base and built up thereon. In some embodiments, the core is preformed, e.g., the core material is preformed to form a preformed core, or the core comprises a cap, and is attached to the base or a post, e.g., by a fastener system or forms a unity piece with the base or post.

In some embodiments, the implant includes at least one anchor which is attached to the implant projecting from the base and adapted to assist in securing a prosthetic device to the dental implant.

Dental implants according to some embodiments of the invention may be installed at locations formerly occupied by teeth having one root or a plurality of roots. Generally, a post is inserted for each root at that location. However, in some embodiments, a post may not be provided for each root. For example, at a tooth location formerly occupied by a tooth having three or more roots, an embodiment may provide for only two posts.

A method according to an embodiment of the invention for installing a dental implant of the type disclosed herein comprises providing a hole or guide hole in a jawbone for each post of the implant positioned to be aligned with each post of the implant in the installed condition of the implant. In some embodiments in which the post(s) are inserted prior to attachment or engagement with the base, the base includes a hole for each post and each hole in the jawbone is positioned to be alignable with a hole in the base. Each post is inserted with an end thereof extending from a respective jawbone hole toward the opposing jawbone a distance sufficient to enter a respective hole in the base or to be attached to or engaged with the base such that the base contacts the jawbone or gum tissue adjacent thereto at the gum line. In the case of a self-tapping post that screws directly into the jawbone without a predrilled hole, no hole or guide hole need be provided, and the post(s) are inserted into the jawbone to be in proper alignment with a hole or holes in the base. A template may be used to properly locate the post(s), which in some embodiments may comprise the base.

In some embodiments in which the base and post(s) are engaged or attached during insertion of the posts, prior to and during insertion of the post(s), the post(s) are movable relative to the base, e.g., are moveably received in holes in the base. As the post(s) are inserted into the jawbone, they engage or become attached to the base and load the base as described above.

In embodiments in which the base and post(s) are attached or engaged prior to insertion of the post(s), each post is inserted into the jawbone (with the base and post(s) attached or engaged), where the base is loaded against the jawbone by operation of a fastener system. In one embodiment in which screw threads are used to insert the post to the jawbone, an attached or engaged base and a single post is rotated as a unit to thread the post to the jawbone and load the base.

In embodiments in which the base is to be installed in direct contact with the jawbone, the gum at the gum line may be cut away to expose the jawbone and provide access thereto for the base to directly contact the jawbone. In embodiments employing a gum line cut, the base is mounted with each post received in a respective hole in the base or attached thereto or engaged therewith and the base in contact with jawbone at the gum line, and the base is loaded against the jawbone, e.g., by operation of a fastener system. In the some embodiments, the jawbone may be cut away to from a recess to receive the base in direct contact with the jawbone.

BRIEF DESCRIPTION OF DRAWINGS

The invention is illustrated in the figures of the accompanying drawings, which are meant to be exemplary and not limiting, and in which like references are intended to refer to like or corresponding parts.

FIG. 3 is a diagram showing in perspective an inserted dental implant of the type depicted in FIG. 1 and an installed dental prosthetic device (a cap) according to an embodiment of the invention, and also teeth next to the implant;

FIG. 4 is a partial cross-sectional view from the side of the inserted dental implant and installed dental prosthetic device depicted in FIG. 3;

FIG. 5 is a diagram showing in perspective an inserted dental implant and an installed dental prosthetic device according to an embodiment of the invention, and also teeth next to the implant;

FIG. 6 is a partial cross-sectional view from the side of the inserted dental implant and installed dental prosthetic device depicted in FIG. 5;

FIG. 7 is a diagram similar to that of FIG. 5 showing in perspective two inserted dental implants and an installed dental prosthetic device (a bridge) according to another embodiment of the invention;

FIG. 8 is a diagram showing a front view of four inserted dental implants and an installed dental prosthetic device for the four lower incisor teeth locations and the two lower canine teeth locations according to an embodiment of the invention; and FIG. 9 is a diagram showing a front view of six inserted dental implants and an installed dental prosthetic device for the four lower incisor teeth locations and the two lower canine teeth locations according to an embodiment of the invention.

DETAILED DESCRIPTION OF PREFERRED EMBODIMENTS

The embodiments of the dental implants 10, 10a, 10b, 10c, 10d and 10e, respectively depicted in FIGS. 1, 10, 11, 14 and 17, each comprise at least one post 12 (or 12a, 12b, or 12c) and at least one base 14.

Figure 17:
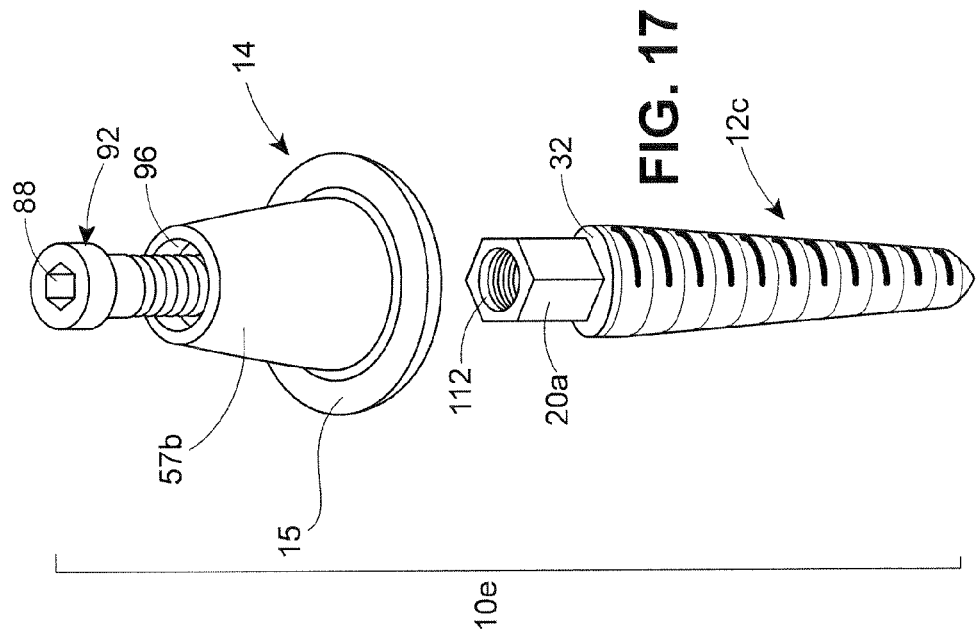
FIG. 17 is an exploded perspective view of a dental implant according to another embodiment of the invention which, similar to the embodiment depicted in FIG. 1, includes a single post.

The base 14 may be configured as described above and in the illustrated embodiments comprises a base plate which in the embodiment of FIG. 17 is part of a cap that is adapted to receive a prosthetic device. In some embodiments, e.g., the embodiments depicted in FIGS. 1, 2, 10, 11 and 14, the base comprises a plate or platform 14 that includes opposed major sides and at least one minor side. In the embodiments depicted in FIGS. 1, 2, 11 and 14, a separate core 42 or cap 57a is attached to the base. In the embodiment depicted in FIGS. 10 and 17, a cap 57 forms a unitary piece with the post 12a and/or the base plate 14. In the embodiments depicted in FIGS. 1, 2, 10, 11 and 14, the opposed major sides 15 of the base 14 are parallel and the at least one minor side 17 is transverse, e.g., generally normal, to the major sides. In the embodiment depicted in FIG. 17, a major side 15a of the base is partially covered by an attached cap 57a. Other configurations and shapes of bases may be used. For example, the major sides may be generally parallel or sloped relative to each other, or include multiple portions which intersect at a vertex or vertices, and the minor sides may not be parallel, but sloped relative to each other, or include multiple portions which intersect at a vertex or vertices. As a general matter, the base may be of generally solid rectangular or trapezoidal configuration (e.g., see FIG. 4), or disc-like (e.g., see FIGS. 11 and 14), or of other solid configuration or cross-sectional shape, e.g., circular, oval, triangular, etc. According to embodiments of the invention, the platform is generally plate-like or disc-like where the thickness is substantially less than the area of either major side. According to embodiments of the invention, the base will have a size and configuration (e.g., perimeter or circumference, surface area, thickness, shape) depending upon the implant location and patient characteristics.

As discussed above, the base 14 provides sufficient supporting surface area for a prosthetic device (or other device) even though the size of the post(s) 12 is relatively small, e.g., typically smaller than that of a post previously used for an implant at a particular implant location. A base loaded against the jawbone according to embodiments of the invention allows the use of a post or posts of smaller diameter and yet the base and smaller post(s) cooperate to provide support for a prosthetic device of the same size as previously used at a particular tooth location. The combination of a base and a plurality of smaller posts, or a base and a single post, provides improved support for a prosthetic device of the same size used previously at a particular tooth location, and the base 14 loaded against the jawbone provides improved support and resistance to a load presented by a prosthetic or other device attached to the implant, and distributes the load.

Figure 1:
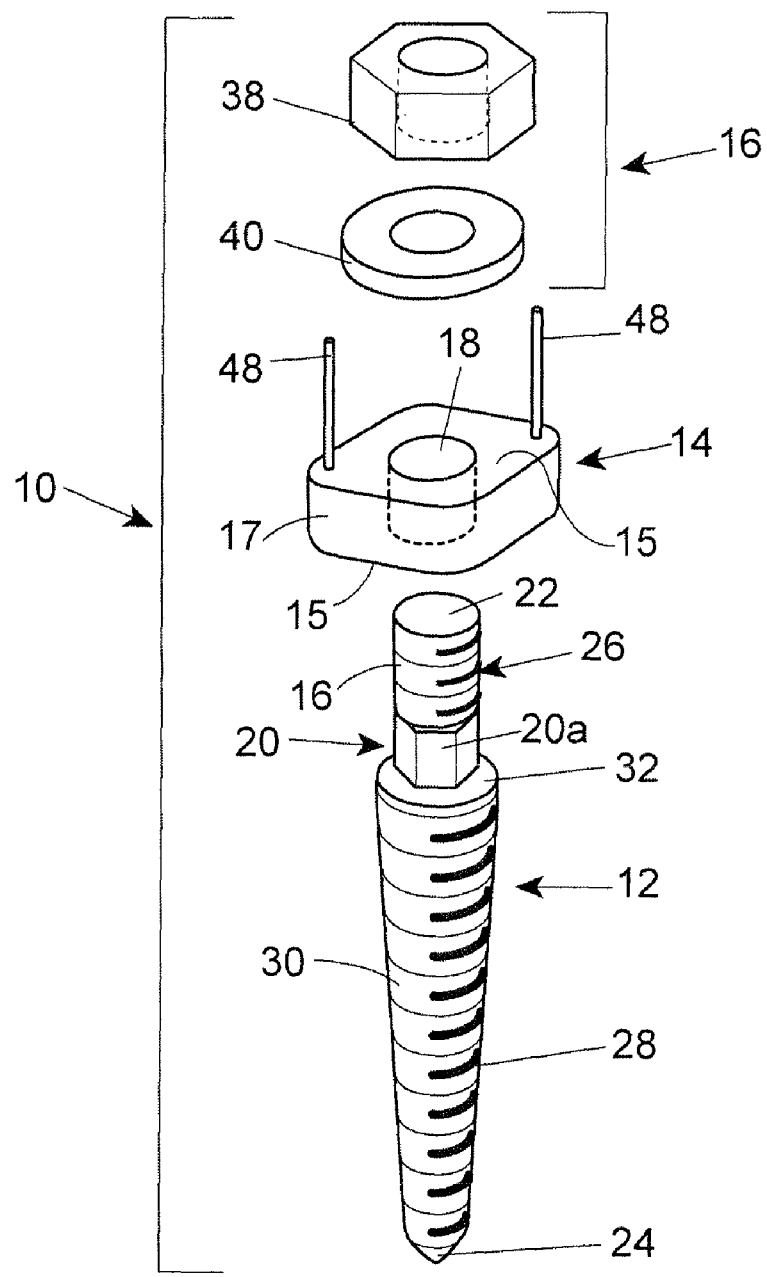
FIG. 1 is an exploded perspective view of a dental implant according to an embodiment of the invention which includes one post.
Figure 2:
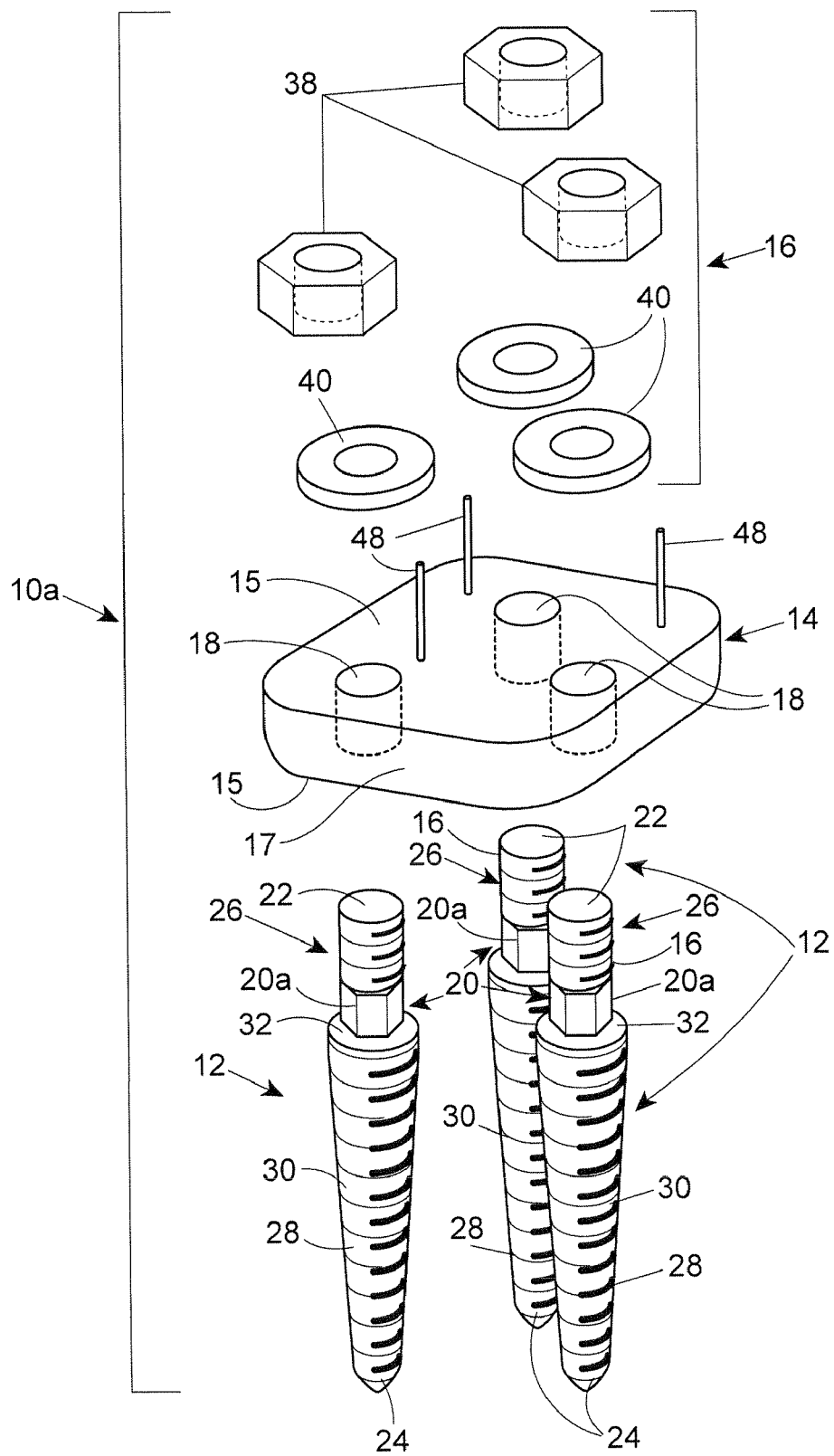
FIG. 2 is an exploded perspective view of a dental implant according to another embodiment of the invention which includes three posts.

In the embodiments depicted in FIGS. 1 and 2, a fastener system, referenced generally by 16, is associated with a post or posts 12. Each of the platforms 14 includes a through hole 18 for a respective post 12. The respective hole 18 and an intermediate portion 20 of each post 12 between the upper end 22 and the lower end 24 of the respective post where the respective post passes through the respective hole in the installed condition of the respective implant (see FIGS. 4 and 6) are complementarily configured, where the size of the respective hole is slightly larger than the size of the respective post portion to provide a snug fit of the respective post in the respective hole. In some embodiments, the hole or holes 18 in the platform are not threaded. In such embodiments, the intermediate portion 20 of the post may or may not be threaded. Either or both the upper portion 26 and the lower portion 28 of the respective posts 12 are configured to allow the respective post to be passed through the respective hole during insertion of the particular implant. In the embodiments depicted in FIGS. 1 and 2, the post 12 includes a shoulder 32 at the transition between the lower portion 28 and the intermediate portion 20. Hexagonal wrench surfaces (or faces or flats) 20a are provided in intermediate portion 20 adjacent shoulder 32, which facilitate wrenching and insertion of the post. As discussed herein, many post configurations other than those illustrated in FIGS. 1 and 2 may be used.

Figure 4:
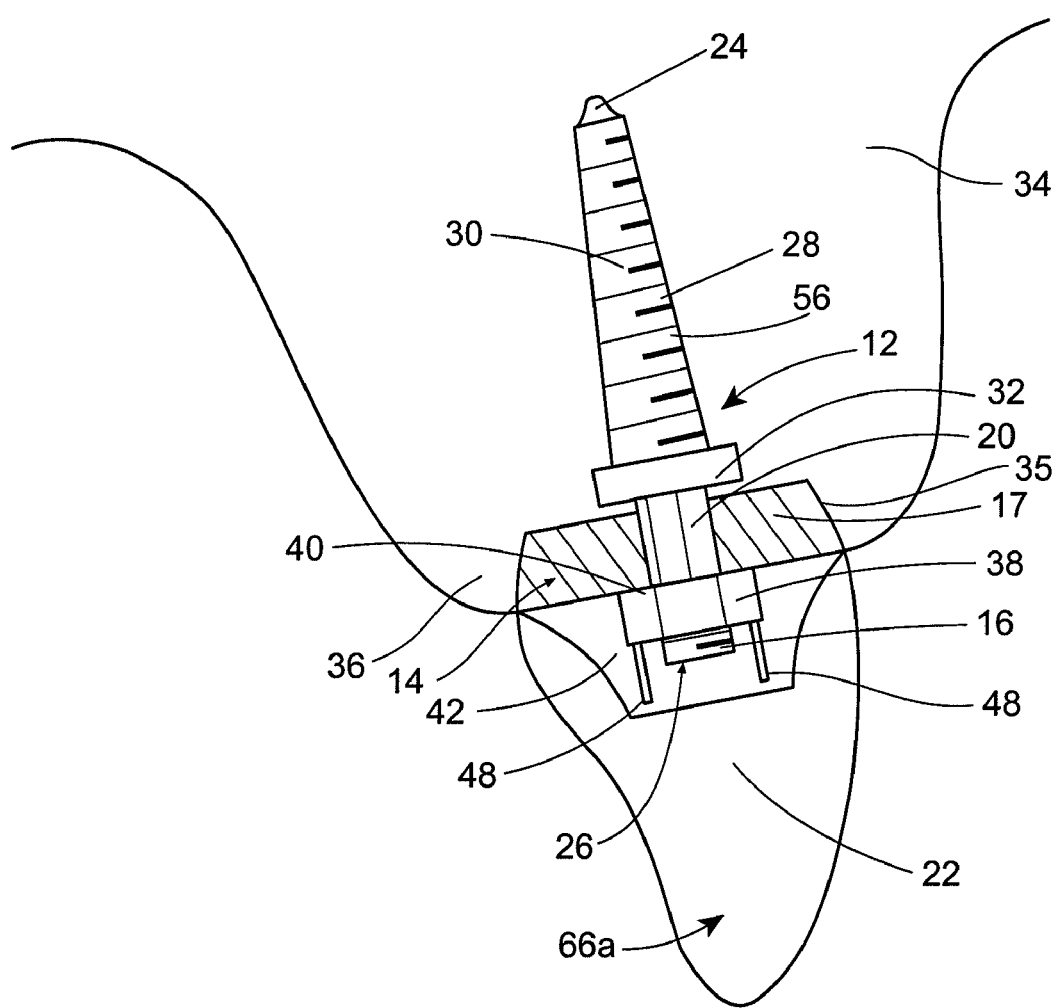
Figure 6:
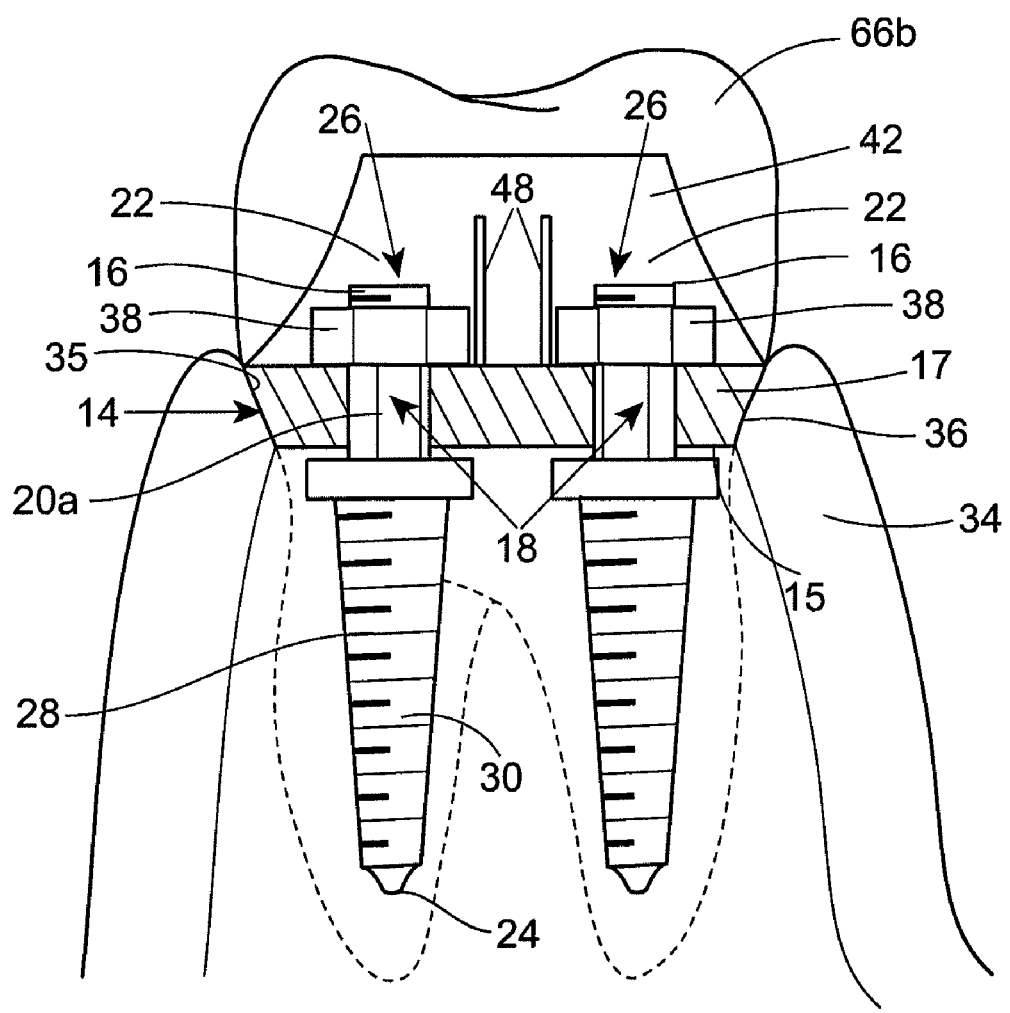

In the installed condition of the implant 10, the platform 14 rests on or otherwise contacts and is loaded against the jawbone 34 at the gun line 36 (see FIGS. 4 and 6). When the platform is loaded against the jawbone through gum tissue, it is preferred that the gum tissue should not be soft tissue. Forcing the platform directly against the jawbone puts pressure on the bone, which maintains bone structure and avoids or reduces drift of the implant, as well as promoting bone growth and bonding of the base to the jawbone. This arrangement can prevent or reduce growth of soft tissue between the platform and the bone, which could otherwise lead to irritation or and/or bleeding, and can also promote gingival health. The platform may be provided with micro-serrations, for example, micro-serrations 107 shown in FIGS. 13-16, which can assist bone growth and bonding.

In the embodiments depicted in FIGS. 1 and 2, each of the posts 12 includes a thread 30 that extends at least along the lower portion 28 of the respective post, but may extend in other portions of the post (or additional threads may be provided) depending upon the fastener system 16 to be used and the configurations of the respective hole 18 and post intermediate portion 20. If the selected fastener system 16 includes threads on the upper portion 26 of the post, such threads may be separate from or related to (e.g., a continuation) of thread 30. In the embodiments depicted in FIGS. 1 and 2, the fastener system 16 comprises a nut 38 that is threaded to the upper portion 26 of the post. Although a pre-threaded system is preferred, in some embodiments, a self threading system may be used, e.g., either the post upper portion 26 or the nut 38 are not threaded and threads are created when the nut is "threaded" to the post upper portion. The fastener system 16 may include a counter-rotation feature to resist loosening, e.g., a lock washer 40, or a retention nut, or double nut (not shown).

Figure 3:
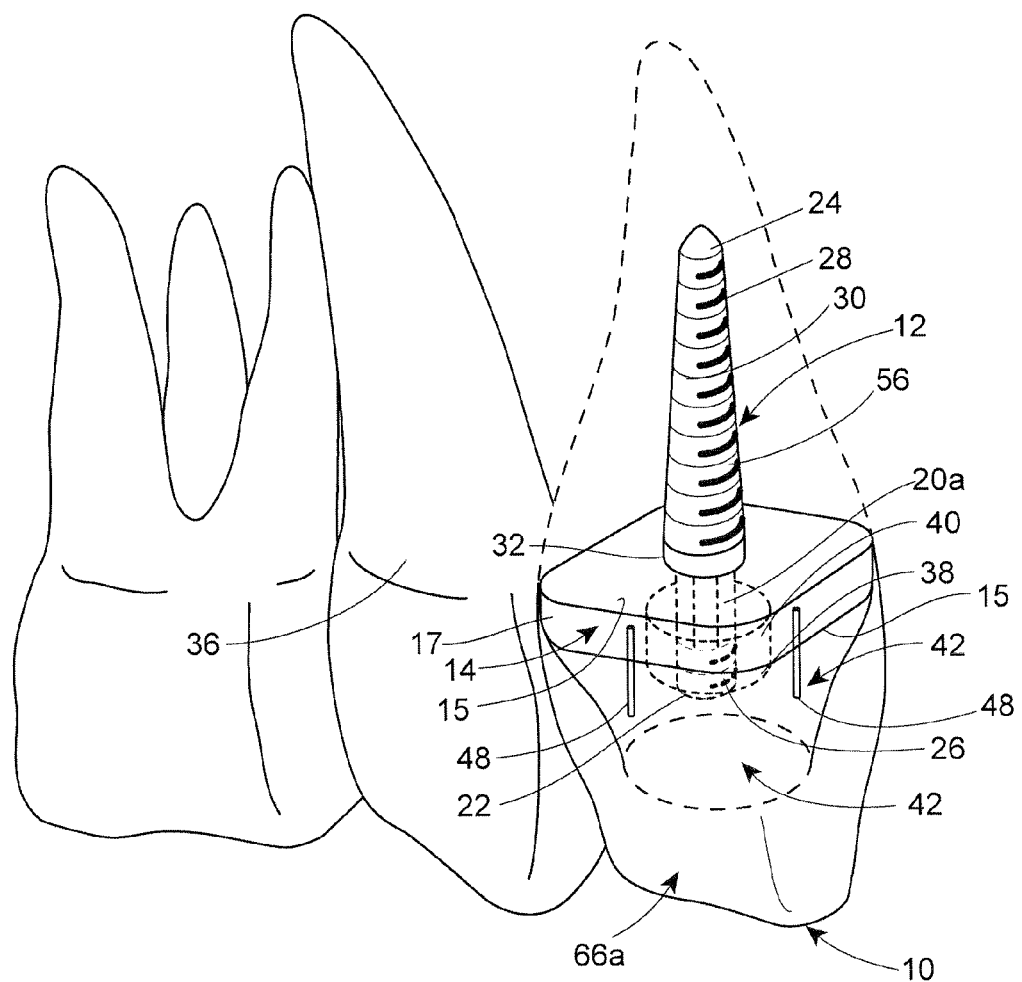
FIGS. 3-9 are illustrations, somewhat schematic, of implants installed in a mouth, specifically.

For use with fixed prosthetic devices, a core 42 (see FIGS. 3 and 4) is built up surrounding the nut to accept the fixed dental prosthetic device, as described in more detail below, and can also hold the nut in place. Alternatively, as discussed below, a core 42 may be preformed or a core in the form of a cap 57, 57a, 57b (FIGS. 10 11, 14 and 17) may be used. Embodiments of the implant 10 may also include one or more anchors 48 used to assist in securing a fixed prosthetic device to the implant 10. Anchors 48 may be configured and attached to the implant 10 in any suitable manner. In the particular embodiment illustrated in FIGS. 1 and 2, an anchor 48 comprises one or more posts attached to or forming part of the platform 14. A post 48 may be attached to the platform 14 extending from the top surface thereof or at an edge, and may extend normal to the top surface of the of the platform or at an angle thereto. For example, a post extending from or adjacent an edge may be angled to extend inwardly relative to the platform, and a post extending close to an edge of the nut 38 may be angled to extend outwardly relative to the platform. As depicted in FIGS. 3 and 4, a post or posts 48 extend so that they can be embedded in the core 42 and possibly also in dental cement used to secure a prosthetic device to the implant.

The anchor may be attached to the platform in any suitable manner, e.g., by means of threads, suitable bonding technologies, e.g., adhesives or cements, ultrasonic, soldering, or welding, etc. For example, an end part may be inserted into a blind or through hole in the platform and attached as just described or by other suitable methods. A platform 14 may be formed with one or more posts 48 extending therefrom by any suitable technology, e.g., stamping, milling, casting or otherwise molding, etc.

In another embodiment, an anchor includes a base portion and a tab portion extending at an angle from the base portion. The base portion includes a hole therethrough and is mounted in the implant on the platform 14 with the upper portion of the post 12 passing through the hole, with the tab portion extending upwardly with at least a portion thereof exposed so it can be embedded at least in the core 42 and possibly also in a dental cement used to secure a prosthetic device to the implant. For example, for an anchor 48 having a base portion that extends beyond the outer periphery of the nut, the angle at which the tab extends from the base can be about 90°, but can be any suitable angle that provides for the tab to extend above the platform spaced from the nut and/or the post sufficiently to be embedded in the core and possibly in the dental cement used to secure a prosthesis to the implant. For example, for a base portion that extends just slightly beyond the outer periphery of the nut, the angle may be larger that 90° to provide clearance between the nut and the anchor tab.

Anchors may be made of any suitable material, e.g., the same material as the platform.

FIGS. 3-7 illustrate examples, somewhat schematically, of inserted dental implants with installed prosthetic devices. Methods of inserting the dental implants will be discussed below.

For example, FIG. 3 illustrates a dental implant 10 of the type depicted in FIG. 1 implanted in the upper left, second incisor tooth position. For context, an outline of the second incisor tooth formerly at the depicted location is illustrated in FIG. 3 by broken lines, and the canine and first molar teeth are also shown. FIG. 4 illustrates a recess 35 in the jawbone 34 that receives the platform or base plate 14. The implant 10 depicted in FIGS. 1 and 3-4 is inserted as follows. A topical or local anesthetic is applied. (In most cases, the patient will not need full anesthesia, i.e., will not need to be put asleep.) The platform rests in the recess on and is loaded against the jawbone 34 at the gum line 36, as discussed above. In cases where direct contact is desired, the gum tissue (e.g., 3 mm-4 mm in thickness) is cut away at the gum line 36 where the platform would otherwise contact the gum. The jawbone may be cut away to form a recess 35 for the base. A gum line cut for the platform may be made before or after the post is inserted. One way to locate the portion of the gum to be cut away is to place the platform in the position in which it would be installed and punch the platform against the gum to create a cut in the gum. In cases where the platform is to be loaded against the jawbone through gum tissue, the presence of soft tissue at the gum line may indicate the need for a gum line cut or other procedure. In some embodiments, the jawbone may be cut away to form a recess to accept the base.

The location of the hole 56 (FIGS. 3-4) in the jawbone 34 for the post is determined depending upon, for example, tooth location and patient characteristics and generally corresponds to the root location at the particular tooth location. An MRI can assist in determining the location of the hole for the post. In some embodiments, pilot hole (not shown) (e.g., 3 mm deep) is drilled in the jawbone 34 in conventional fashion to accept the particular post 12 to be used. A template or guide stent (not shown) may be used to drill the pilot hole. In some embodiments, the actual jawbone hole 56 is then drilled. In some embodiments, a self-tapping post is inserted without a guide hole. In some embodiments of the invention, a self-threading system is used, i.e., the jawbone hole 56 is not threaded and a thread is created in the hole when the post 12 is tightened into the hole. Regardless of whether the hole 56 is self-threaded or not, its diameter is slightly less that the OD of the post (including threads). If the jawbone hole 56 is not self-threaded, then the hole is tapped to match the screw thread 30 of the post. The post 12 is threaded to the jawbone hole 56 in conventional fashion. In some embodiments, a self-tapping post is screwed into the jawbone in a guide hole, or directly without a guide hole. As mentioned above, other types of posts may be used, and the insertion procedure depends at least to some extent on the particular post used.

Known wrench systems may be used to tighten a post to the jawbone. For example, a post may first be hand tightened into the jawbone hole, then wrench tightened with two or more wrenches ending with the use of a torque wrench. For example, a hand finger wrench may be used, followed by a wing nut wrench, followed by a 30 Newton torque wrench. The force with which the platform 14 is loaded against the jawbone is sufficient to provide for the support and resistance discussed herein.

The platform 14 is then inserted onto the post 12. For example, the platform 14 is positioned over the post 12 with the post and the hole 18 in the platform 14 aligned and the platform raised (lowered for implantation in the lower jaw) until it abuts the jawbone 34 at the gum line 36. Suitable clearance exists between the platform 14 and the shoulder 32 to facilitate loading of the platform against the jawbone. The platform 14 is positioned so that its upper major surface 15 is level with a line or plane at the concerned tooth location. The implant may include one or more anchors 48 extending above the platform 14.

The fastener system 16 then secures the platform 14 to the post with the platform loaded against the jawbone. As mentioned above, the fastener system 16 used for the implant embodiments depicted in FIGS. 1 and 2 comprises a nut 38 threaded onto the upper portion 26 of the particular post 12. After the lock washer 40 has been seated on the post 12, the nut 38 is initially loosely threaded to the post upper portion 26 until the platform is seated against the jawbone. The nut is torqued to a predetermined tension, e.g., 35 Newtons, using a conventional torque wrench to load the platform against the exposed jawbone. Different wrenches may be used to tighten the nut to the post before using the torque wrench to tighten the nut to the predetermined tension.

For the embodiments depicted in FIGS. 1, 2, 3 and 4, the core 42 is applied over the nut 38 and the anchors 48. As illustrated in FIG. 4, the core completely covers the nut and the anchors. However, part of the nut and/or the anchors and/or the top portion of the post may remain exposed to be embedded in a dental cement used to secure a prosthetic device to the implant. The core 42 may be built-up using glass polymer, silicon beads, resin, composite and/or metal, or any other suitable material or materials. This may be done manually or the core can be pre-formed and installed as a prefabricated core, which can include pre-drilled holes for the nut and the anchors. A prefabricated core may be cemented to the nut and anchors or attached by a fastener system or be part of the base or a post. Use of a prefabricated core facilitates installation, particularly in the back of the mouth. The installed core is sized to leave space to be filled by a dental cement to attach a prosthetic device to the implant. In the embodiment depicted in FIG. 3, the core can be provided with a taper, e.g., 7°, to provide space between the core and the interior of the prosthetic device to apply cement. The outer surface of the core 42 may be grooved to promote adherence thereto of the cement.

The foregoing implantation procedures may be carried out during a single visit or multiple visits depending primarily upon site preparation requirements, e.g., whether a tooth extraction is involved. In most instances, the procedure can be performed in a single visit, even where a tooth is extracted during that visit. At the same that the implant is installed, or in a subsequent visit, preparation is made to mount a dental prosthetic device to the implant. The prosthetic device for implant 10 may be a cap 66a (FIGS. 3-4), or a crown 66b (FIGS. 5-6) for implant 10a replacing a single tooth, or a bridge 66c (FIG. 7) anchored to one dental implants 10a and either an existing tooth or another dental implant 10a and bridging one or more teeth positions, or fixed partial (or full) prosthetic device 66d-e (FIGS. 8-9) to be anchored to two or more implants 10 or 10a or at least one implant 10 or 10a and at least one existing tooth. The prosthetic devices 66a-e are otherwise conventional and may be made conventionally.

Preparation to mount a dental prosthetic device includes obtaining impressions in conventional fashion and providing them to the prosthesis manufacturer. The prosthetic device is typically custom made to fit the mouth and may involve milling for an exact fit. With respect to a cap 66a for the second incisor tooth position embodiment illustrated in FIGS. 3 and 4, the cap 66a is seated on the platform 14 extending over the minor sides 17 down past the gum line 36. Therefore, the impressions for the cap 66a are taken down to the gum line 36 past the platform sides 17 of the platform 14.

In some instances, an impression can be taken and the prosthetic device made prior to installation of the dental implant. In such cases, the dental implant and the appropriate prosthetic device can be installed in the same visit. In cases where the prosthetic device is to be installed in a visit subsequent to installation of the implant, a temporary prosthetic device (e.g., a conventional temporary cap, not shown, but in configuration similar to cap 66a) may be installed using a temporary cement. As for a permanent installation described below, the cement fills all of the interior of the cap and embeds the core 42 and any exposed portion of the anchors 48, the nut 38 and the upper post portion 26 to temporarily secure the temporary cap to the dental implant 10.

When the permanent cap 66a is ready, the temporary cap is removed if one has been installed, any needed preparation is performed, the cap 66a is tested for fit and any adjustments are made, etc., before final installation. The cap 66a is then installed using permanent cement which fills all of the interior of the cap 66a and embeds the core 42 and any exposed portion of the anchors 48, the nut 38 and the upper post portion 26 to permanently secure the cap to the dental implant 10. Installation includes proper seating and positioning of the cap 66a over the platform 14 and against the jawbone 34, etc., as depicted in FIGS. 3 and 4.

Figure 5:
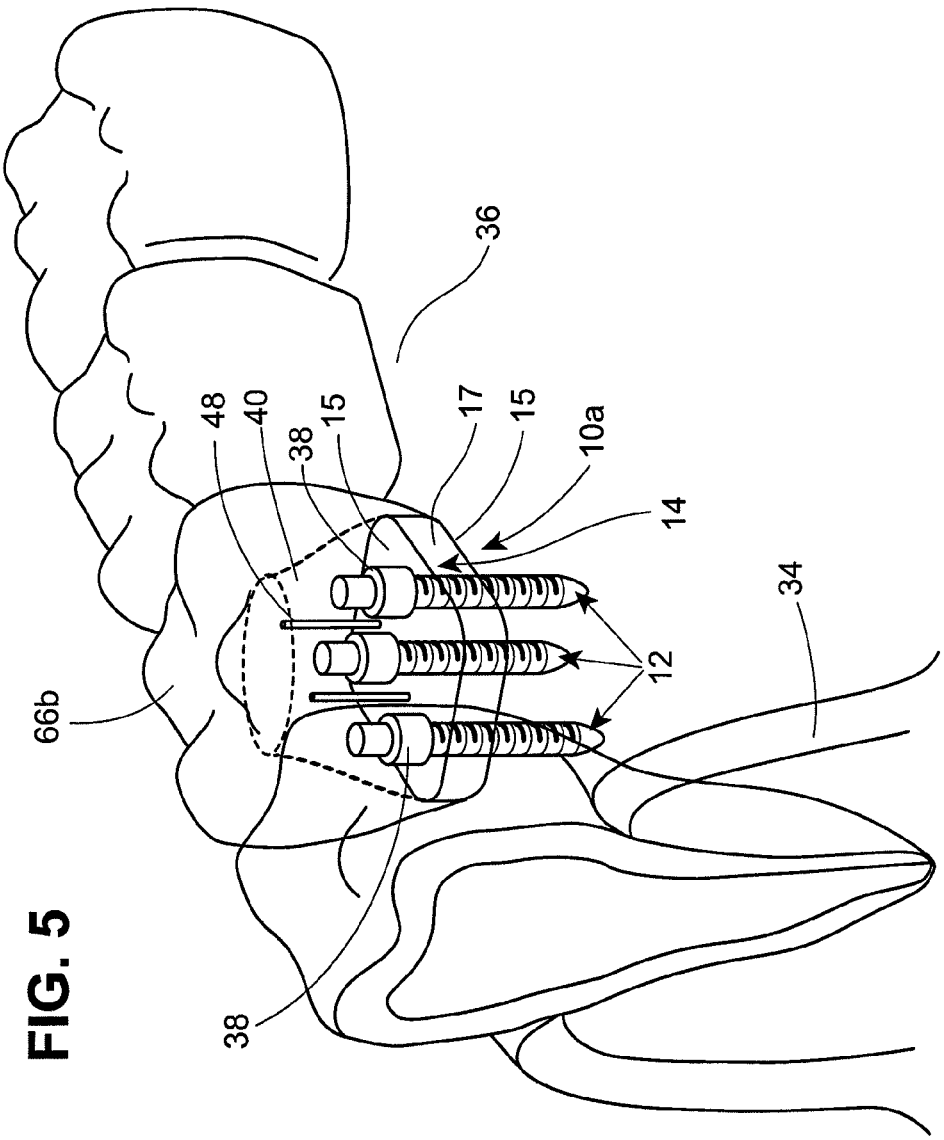

The dental implant 10a illustrated in FIGS. 2 and 5-6 includes three posts 12 and is implanted in a molar tooth position. In FIG. 6, the broken lines illustrate roots of a tooth formerly at that location. The description above for the single post implant 10 of FIGS. 1 and 3-4 generally applies to the multi-post implant 10a of FIGS. 2 and 5-6, including the discussions relating to posts, platforms and fasteners systems, except that post and platform sizes may differ and the platform 14 has a hole 18 for each post. Thus, the description above applies generally to posts 12, platform 14, nuts 38 and anchors 48 of the embodiment of FIGS. 2 and 5-6.

The installation procedure for the multi-post implant 10a is also similar to that for the single post implant 10. After site preparation, generally as described above, a hole 56 is drilled in the jawbone 38 in conventional fashion to accept each of the particular posts 12 used. The positions of the holes 56 correspond generally to the root positions at the tooth location, and are selected based on site conditions.

After the posts have been inserted, the platform 14 is inserted onto the posts 12, e.g., by positioning the platform 14 over the posts 12 with the posts and the holes 18 in the platform 14 aligned and the platform lowered (raised for implantation in the upper jaw) until it abuts the jawbone 34 at the gum line 36. The platform 14 is positioned so that its upper major surface 15 is level with a line or plane at the concerned tooth location. The fastener system 16 is then tightened to secure the platform 14 to the posts loaded against the jawbone, i.e., the lock washers and nuts are applied as described above. The core 42 is applied as described above.

The installation procedure for a multi-post implant, similar to a single post implant, may be carried out during a single visit or multiple visits depending primarily upon site preparation requirements, e.g., whether a tooth extraction is involved, and in most instances, can be performed in a single visit. The dental prosthetic device, a crown 66b in FIGS. 5-6, is installed as generally described above for the cap 66a.

Figure 7:
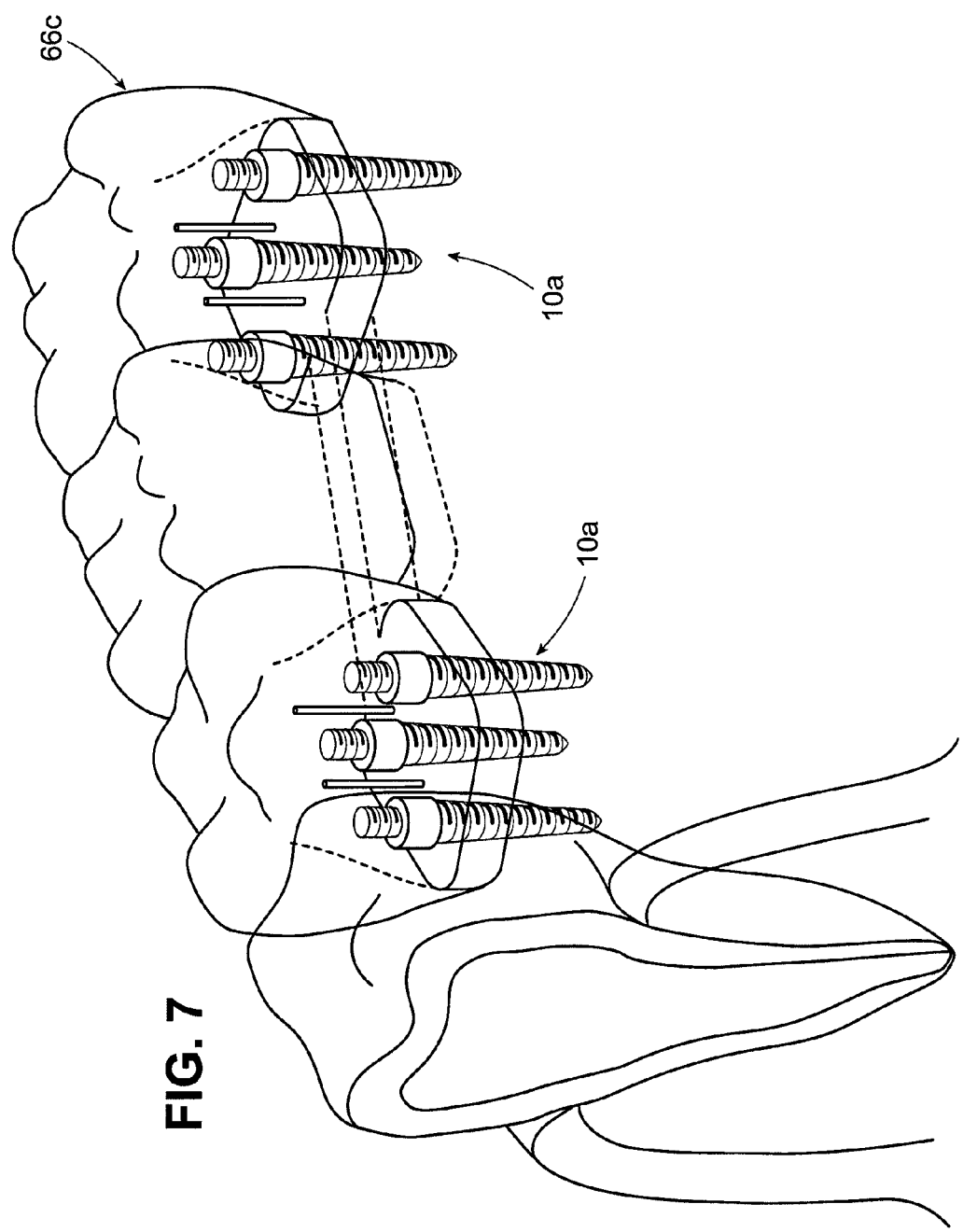

The embodiment depicted in FIG. 7 includes two dental implants 10a of the type depicted in FIGS. 2 and 5-6 and a bridge prosthetic device 66c attached to the two implants 10a. Both implants 10a are implanted as described in connection with FIGS. 3-6. Impressions for the bridge 66c are taken generally as described above, including down to the gum line surrounding each platform and the bridged area. A temporary bridge or two temporary caps may be installed before the permanent bridge 66c. Proper positioning places the top of the bridge 66c in the patient's normal bite line for the concerned area.

Figure 8:
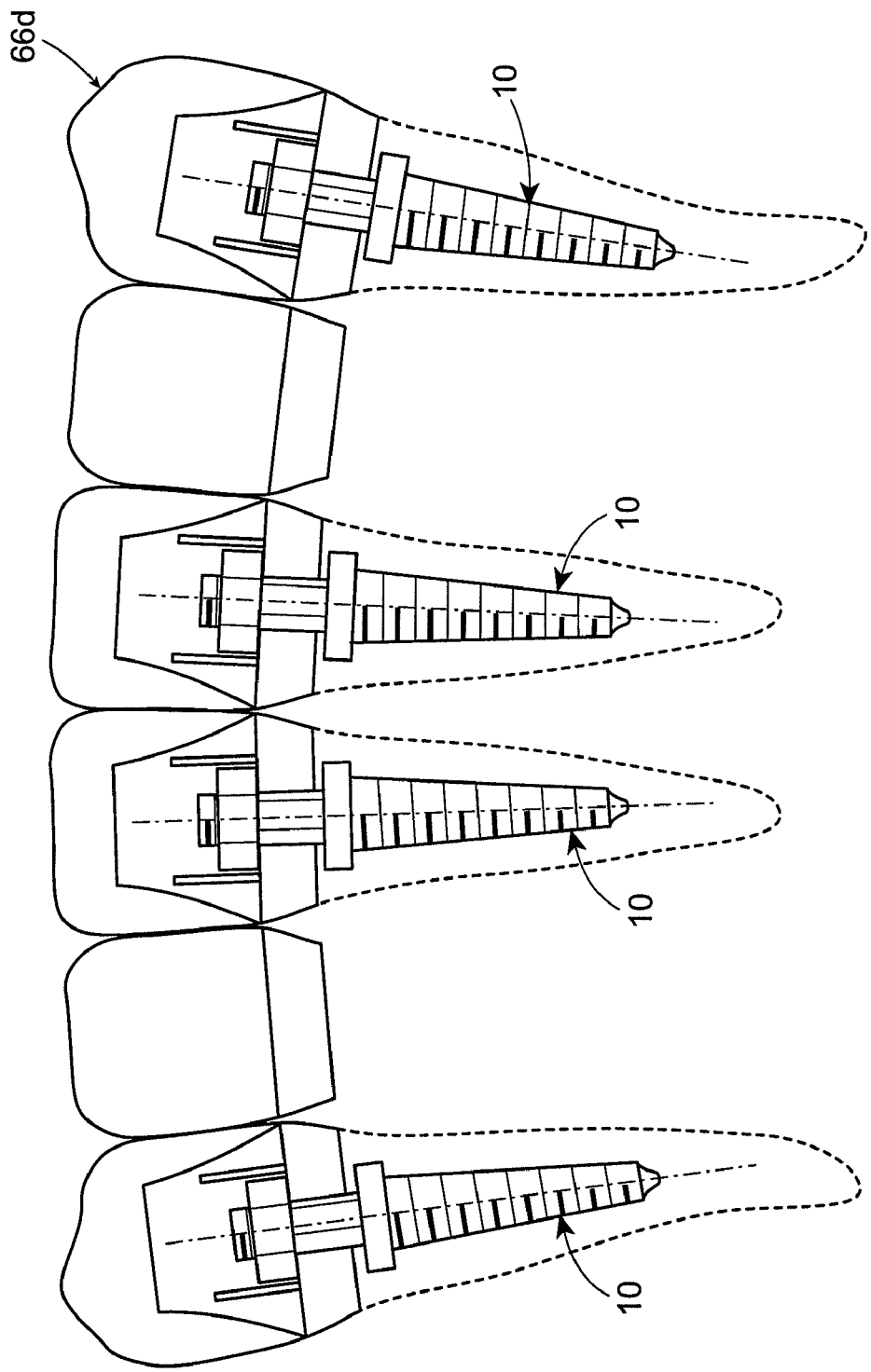
Figure 9:
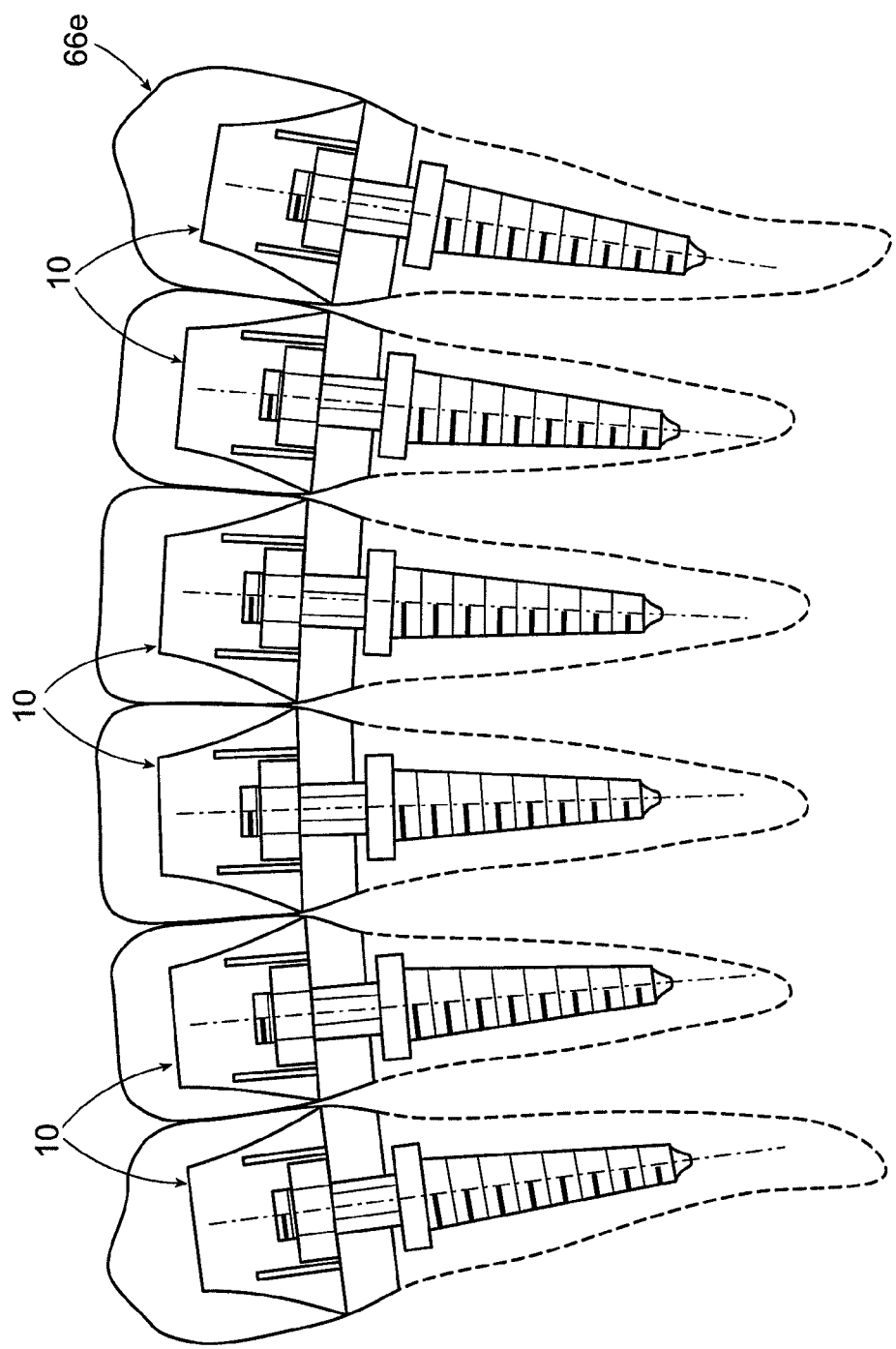

In some embodiments, implants are used to anchor a partial or full prosthesis extending over a number of tooth locations in the same or different quadrants, etc. The embodiment depicted in FIG. 8 provides a prosthetic device 66c covering the lower front teeth positions, i.e., the four incisor teeth and the two adjacent canine teeth. In FIG. 8, the broken lines illustrate part of incisor teeth formerly at the depicted locations. In this embodiment, four implants 10 are used, to for the two center incisor teeth positions and one each for the canine teeth positions. The embodiment depicted in FIG. 9 provides a prosthetic device 66d, similar to the prosthetic device 66c shown in FIG. 8, covering the lower front teeth positions, i.e., the four incisor teeth and the two adjacent canine teeth. In FIG. 9 embodiment, however, six implants 10 are used, one for each of the incisor teeth positions and canine teeth positions. The implants 10 in the FIGS. 8 and 9 embodiments are similar to the implants illustrated in FIGS. 1 and 3-4, and are installed as described above. In FIG. 9, the broken lines similarly illustrate part of incisor teeth formerly at the depicted locations.

Figure 10:
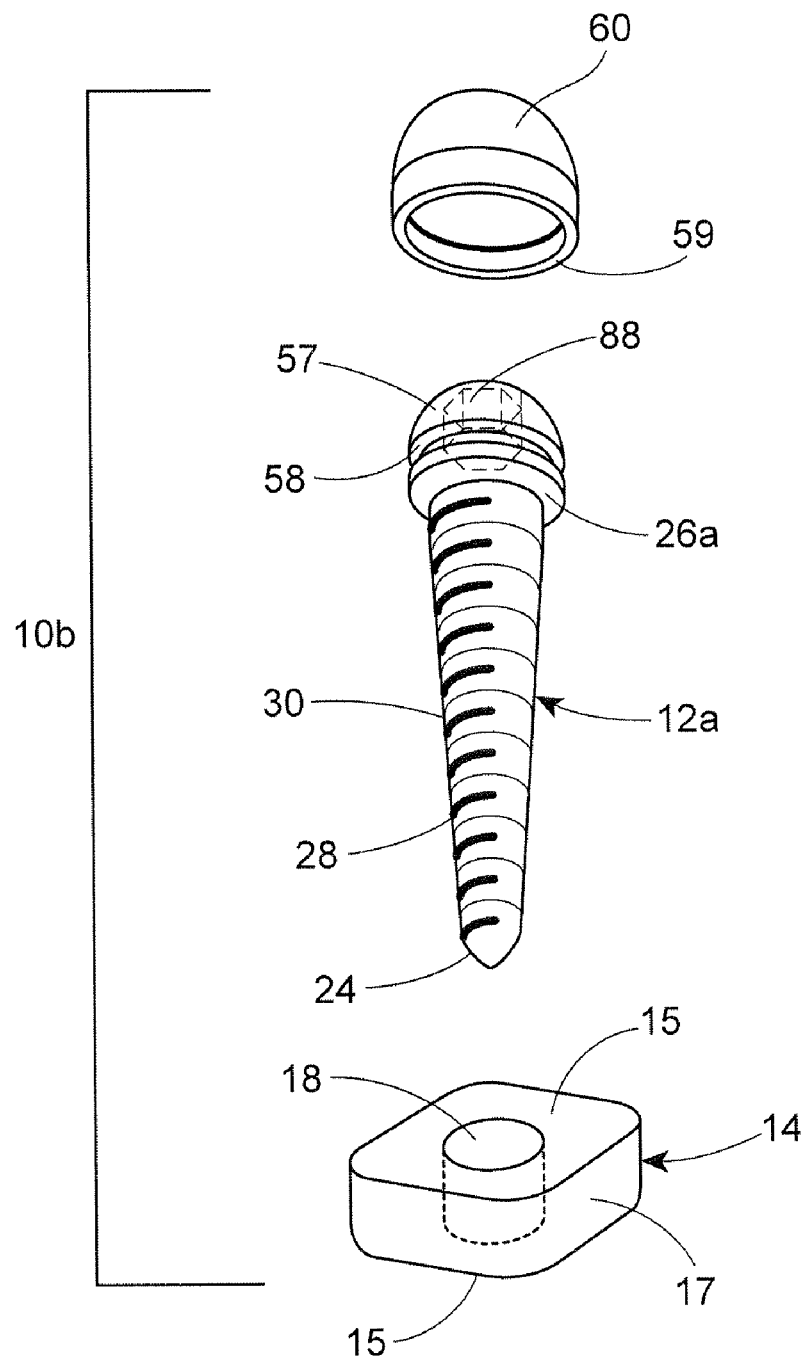
FIG. 10 is an exploded perspective view of a dental implant for a removable prosthetic device according to an embodiment of the invention.

Dental implants 10 and 10a illustrated in FIGS. 1 and 2 are for prosthetic devices of the fixed type. However, dental implants according to embodiments of the invention may also be used for removable dental prosthetic devices. FIG. 10 illustrates a one post embodiment of a dental implant 10b for a removable prosthetic device, e.g., a cap. In a one-post embodiment, e.g., for insertion at a tooth location formerly occupied by a single root tooth (which may be referred to as a mini-implant), the dental implant comprises at least one post 12a, and a base 14. The upper portion 26a of the post 12a terminates in a core in the form of a ball 57. The implant 10b is similar to the one post implant illustrated in FIGS. 1 and 3, except that the fastener system comprises the ball 57 which bears against the top surface 15 of the platform 14. The post 12a is inserted through a base 14 and threaded to the jawbone (using internal wrench surfaces 20a), with the ball 57 bearing against the platform, to secure the post and the base and to load the base against the jawbone. The ball 57 and the removable implant may be conventional, e.g., the ball 57 includes a recess 58 to receive an o-ring 59 within a removable prosthetic device 60 which compresses when the removable prosthetic device is mounted over the ball to removably attach the prosthetic device to the post.

In the implant embodiments 10 and 10a depicted in FIGS. 1 and 2, the post(s) are inserted prior to engagement thereof with the base, which is engaged by means of the fastener system 16 after insertion of the post(s). In the implant embodiment 10b depicted in FIG. 10, the base 14 and the post 12a are engaged during insertion of the post 12a by means of the ball 57 (a fastener part) bearing against the base. In this embodiment, the post 12a and ball 57 function similar to a bolt. In the embodiments depicted in FIGS. 1 and 2, the core 42 is built up on the base, and in the embodiment depicted in FIG. 10, the core, in the form of cap 57, is attached to and forms part of the post 12a. The implant embodiments 10c, 10d and 10e depicted in FIGS. 11, 14 and 17 include a preformed core in the form of a cap 57a or 57b. In the implant embodiments 10c and 10d, the base 14 and the posts 12b are engaged during insertion of the posts into the jawbone, and in the implant embodiment 10e, the base 14 and the post 12c are engaged after insertion of the post.

Figure 11:
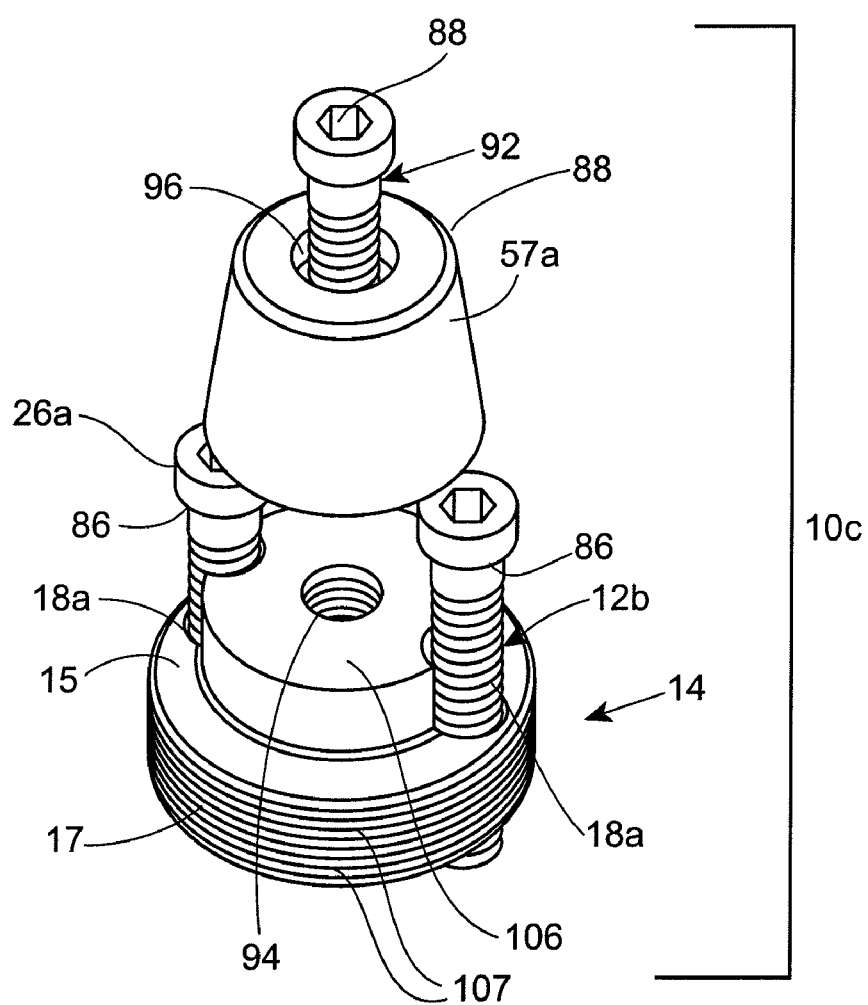
FIG. 11 is an exploded perspective view of a dental implant according to another embodiment of the invention which includes two posts.
Figures 12, 13:
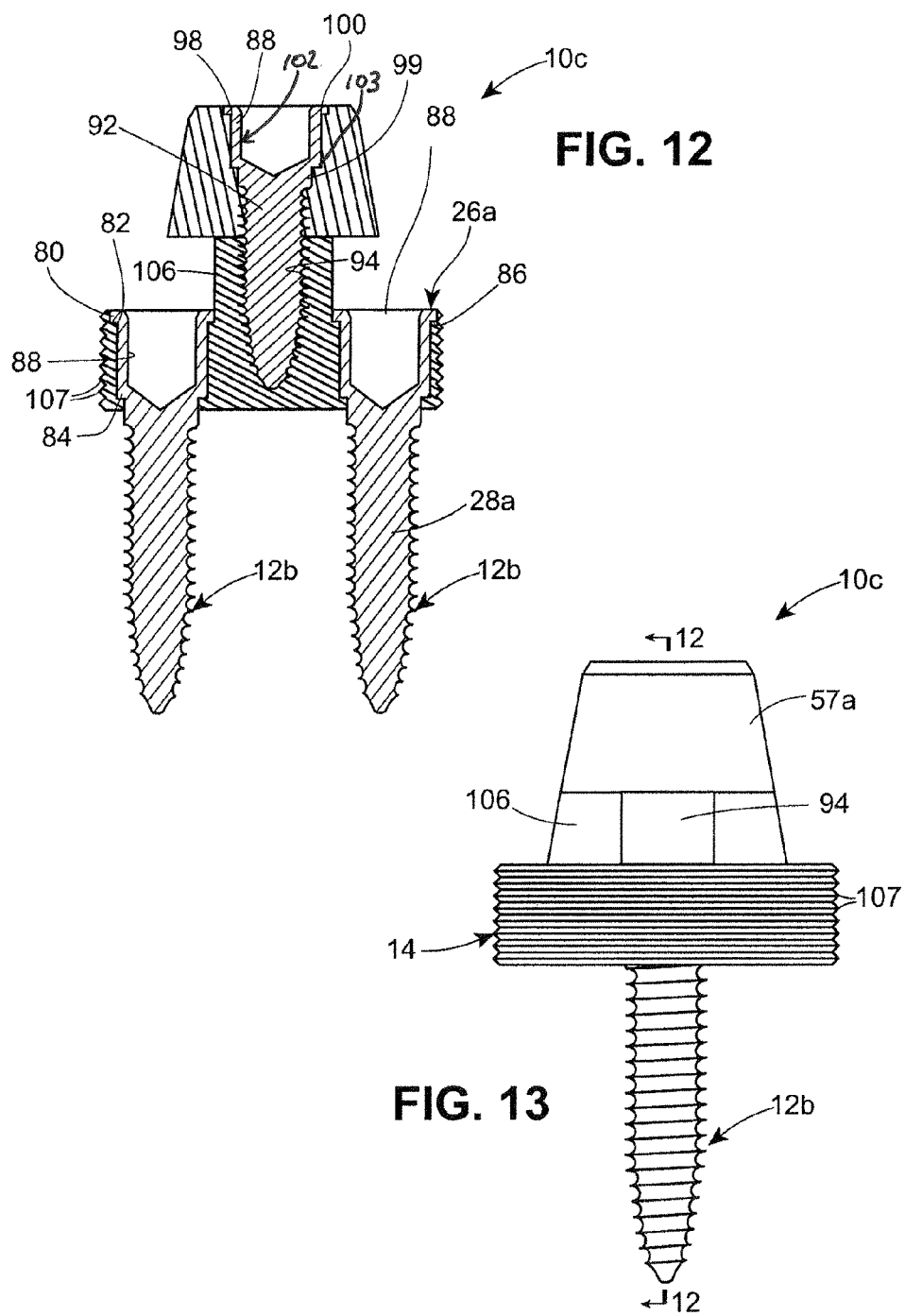
FIG. 12 is a cross section view of the dental implant depicted in FIG. 11 taken along line 12-12 in FIG. 13.
FIG. 13 is a side view of the dental implant depicted in FIG. 11.

The implant embodiment 10c depicted in FIGS. 11-13 includes two threaded posts 12b, a base 14 and a cap 57a. The base 14 includes two holes 18a, one for each post 12b. Each hole 18a (FIG. 12) includes an enlarged diameter portion 80 which forms a shoulder 82 at the transition to a smaller diameter portion 84. Each post 12b includes an upper portion 26a and a lower portion 28a. The lower portion 28a is sized to pass through the smaller diameter portion 84 of a hole 18a, while the upper portion 26a is enlarged to form a shoulder 86 which is sized to engage the shoulder 82 in the hole 18a. The upper portion 26a of the post 12b is recessed and includes wrench surfaces 88 configured to receive a complimentary configured wrench tool (not shown).

The implant 10c also includes a cap 57a that is attached to the base 14 by a fastener system comprising a threaded bolt 92 and a threaded hole 94 in the base 14. The cap 57a includes a hole 96 having larger and smaller diameter portions 98 and 99 (FIG. 12), and a shoulder 100. The bolt 92 includes an enlarged upper portion 102 and a shoulder 103 sized to engage the shoulder 99 in the cap. The bolt 92 also includes internal wrench surfaces 88 by means of which the bolt is tightened to the base 14.

The base 14 includes a central raised portion 106 between the two holes 18a. The cap 57a is tapered in cross section (FIG. 12) generally as described above for core 42. The outer periphery of the base 14 includes micro-serrations 107, which promote bone growth, particularly where a base is inserted in a cut away or recessed portion of the jawbone.

The implant 10c is installed as follows. Guide holes, post holes and any gum cutting is carried out generally as described above. The posts 12b are seated in the holes 18a of the base and the posts are aligned with respective holes in the jawbone and threaded therein and tightened using suitable wrenches. This procedure inserts the posts into the jawbone and with tightening of the posts in the jawbone loads the base 14 as well as the posts 12b. The cap 57a is attached by means of the bolt 92 and threaded hole 94 using a suitable wrenching tool. Depending upon accessibility of the upper portions 26a of posts 12b to a wrenching tool, the cap 57a may be attached to the base prior to insertion of the posts in the jawbone. For example, axially extending grooves in the side of the cap 57a may be provided to give access to the upper portions of the parts 12b.

Figure 14:
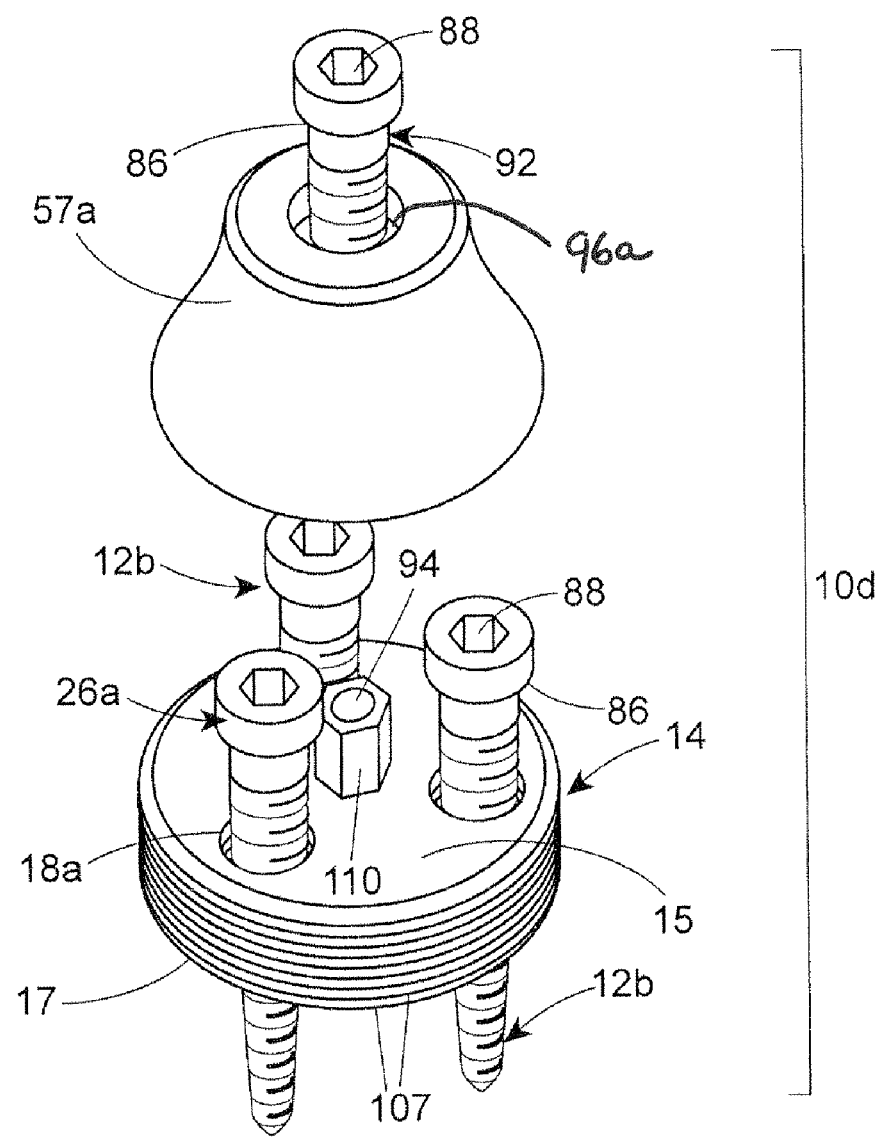
FIG. 14 is an exploded perspective view of a dental implant according to another embodiment of the invention which, similar to the embodiment depicted in FIG. 2, includes three posts.
Figure 15:
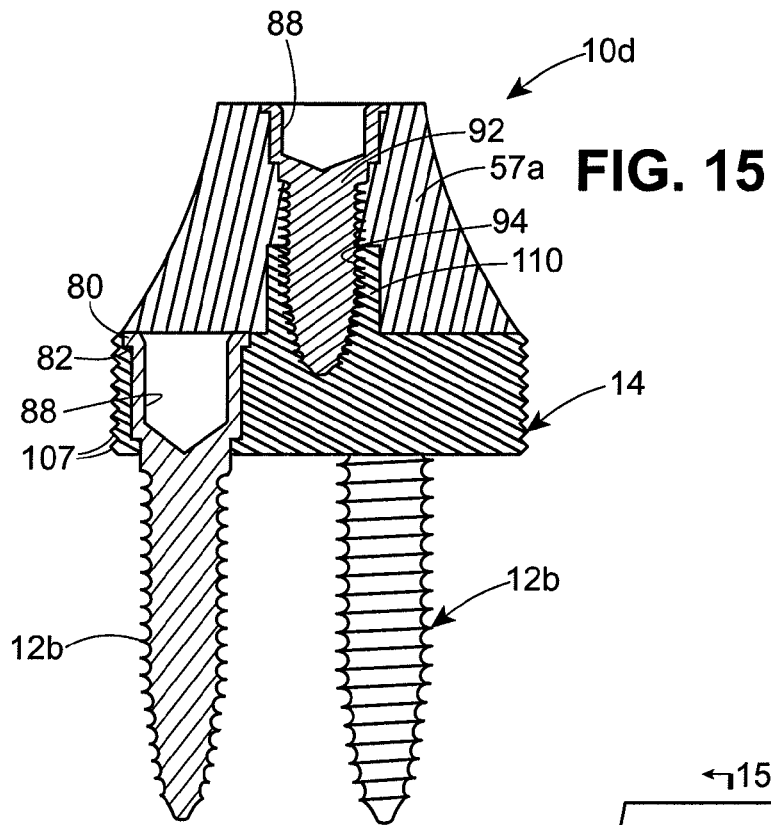
FIG. 15 is a side view of the dental implant depicted in FIG. 14.
Figure 16:
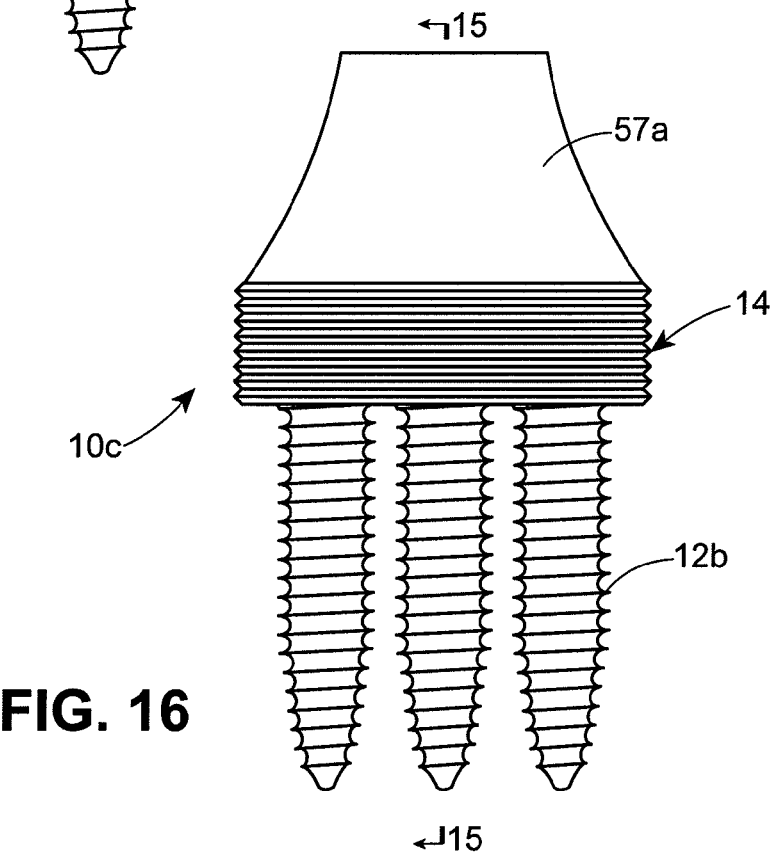
FIG. 16 is a cross section view of the dental implant depicted in FIG. 14 taken along line 16-16 in FIG. 15.

The three-post implant embodiment 10d depicted in FIGS. 14-16 is similar to the two-post implant embodiment 10c depicted in FIGS. 11-13. Threaded bolt 92 is tightened to base 14 to attach cap 57a to the base. The hole 94 provided for the threaded bolt 92 used to secure the cap 57a to the base 14 is implemented by an internally threaded post 110 attached to the base. The cap 57a includes a central axially extending hole 96a that receives the post 110, and the cap 57a covers the upper portions 26a of posts 12b. Thus, the cap 57a is attached after the posts are inserted. However, grooves or structure may be provided in a cap 57a to permit a wrenching tool to access the upper portion 26a of posts 12b to tighten them to the jawbone. This would allow the cap 57a to be attached before the posts are tightened to the jawbone.

As depicted in FIGS. 11-13, the cap 57a is supported on the base 14 in the mounted configuration of the implant depicted in FIG. 13. As described above in connection with mounting a prosthetic device to core 42 supported by base 14 of the implant embodiment of FIGS. 3-4, cap 57a accepts a prosthetic device (not shown in FIGS. 11-13). The diameter of the cap 57a at its base is less than the diameter of the base 14, so that the cap overlays a first inner portion of the base but not a second outer or peripheral portion of the base. Therefore, a prosthetic device received on the cap 57a entirely overlays the cap 57a and the inner portion of the base, and also overlays the outer portion of the base and extends thereto. The cap 57a is attached to the base 14 by bolt 92 as depicted in FIG. 12. As such, the entire surface area of the cap 57a including the hole 96 and the bolt 92 therein (FIG. 11) are entirely supported by the base 14. A prosthetic device attached to the cap 57a is therefore entirely supported by the base 14.

The cap 57a in the embodiment of FIGS. 14-16 is supported as described for cap 57a in FIGS. 11-13, except that the diameter of the base of cap 57a in FIGS. 14-16 is the same as the diameter of the base 14, and the cap 57a entirely overlays the base 14. Therefore, a prosthetic device attached to the cap 57a is entirely supported by base 14 as described above for the embodiment of FIGS. 11-14, except that the cap 57a in FIGS. 11-13 entirely overlays the base 14.

Figure 19:
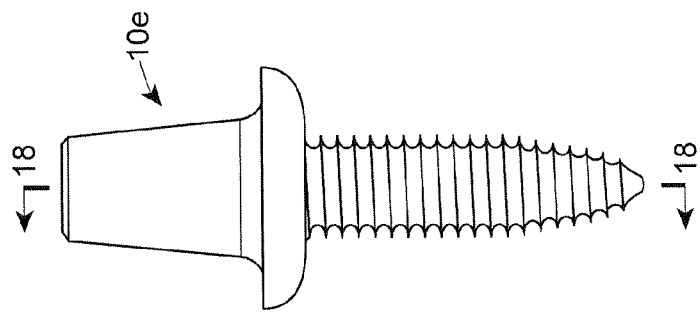
FIG. 19 is a cross section view of the dental implant depicted in FIG. 17 taken along line 19-19 in FIG. 18.
Figure 18:
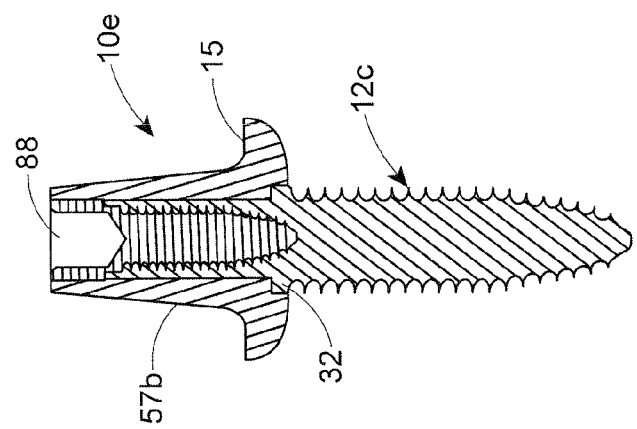
FIG. 18 is a side view of the dental implant depicted in FIG. 17.

In the embodiment of FIGS. 17-19, as mentioned, the cap 57b and the base 14 are attached, and a prosthetic device is attached to the cap 57a. The lower diameter of the cap 57a is smaller than the diameter of the base 14, similar to the embodiment of FIGS. 11-13.

The single post implant 10e depicted in FIGS. 17-19 includes a post 12c and a base 14 which includes a cap 57b attached thereto. In one embodiment, the post 12c and the base with attached cap are separate pieces attached together by a fastener system comprising a threaded bolt 92 and an internally threaded hole 112 in the upper portion 26b of post 12c, as illustrated in FIGS. 17 and 18. The post 12c is configured similar to the post 10 in that it includes a shoulder 32 to engage the base 14 (within the cap 57b). The implant 10e is installed similar to the implant 10, except that the bolt 92, instead of a nut, attaches the base to the post 12c and loads the base and the post. The cap portion 57b is tapered, as discussed above. In an alternative embodiment, the base 14, including the cap portion 57b, may be attached to the post 12c, either as a unitary piece or by a fastener system. In this embodiment, the assembled implant would appear as shown in FIG. 19. The post 12c with attached base and cap is installed into the jawbone as a unit, e.g., by rotating the unit to thread the post 12c to the jawbone. In this embodiment, the wrench surfaces 88 in the upper portion of the bolt 92 may be used to tighten the unit to the jawbone. In an embodiment in which the base/cap and the post are a unitary piece, wrench surfaces 88 may be provided internally or externally in the cap portion.

The sizes and configurations of the dental implants 10, 10a illustrated in the drawings may vary depending upon, e.g., the tooth or implant location in which the particular implant is inserted, and patient characteristics. Generally, the posts are tubular and the diameter of the post decreases or tapers down towards the lower end 24 of the post, e.g., the lower portion 28 is generally frustoconical. The entire post may be threaded or only portions thereof, as illustrated. Depending upon the particular fastener system, the upper portion of a post may be tubular and threaded (where the fastener system includes a threaded nut), and the intermediate portion may be tubular or of rectangular or other cross sectional shape (e.g., hexagonal forming wrenching surfaces). Or the upper portion may include a screw head or bolt head (e.g., posts 12b and 12c in FIGS. 11 and 14). The lower portion may be tubular or generally conical or frustoconical and threaded. In some embodiments, the post may include stepped portions, or may be splined or splintered, or include structure other than or in addition to a thread to secure the post to the bone. For example, a post may be press-fitted to the jawbone rather than threaded. Many suitable post configurations other that those illustrated may be used and will be known to those working in this field. As discussed above, a post may be entirely self-tapping, i.e., not require a guide hole, or self-tapping in a guide hole.

The configuration, e.g., size (diameter and length) and shape of the particular post may vary depending upon the tooth or implant location at which the post will be implanted, characteristics of the particular patient, and other factors which may arise on an implant-by-implant and patient-by-patient basis. Generally, a post is implanted for each root of the tooth at the tooth location in which the implant will be implanted, e.g., one post for the incisor and canine tooth positions and two or three posts for the molar tooth positions.

The posts generally are made of a non-corrosive material or materials and have a high tensile strength. For example, a titanium post is suitable. The posts may be coated as known in the art, for better adhesion to bone. The particular length and diameter of the post(s) depends on a number of factors such as tooth or implant location and patient characteristics. The size of the nut (OD) or screw head can be about ⅛ to about ½ the size of the platform (a cross dimension, e.g., diameter of the platform). The lower portions of the posts have thread sizes previously used for dental implant posts, and the upper portions have the same or similar threads. The nuts have threads that mate with those on the upper portion of the posts.

The platform is similarly made of a non-corrosive material or materials, e.g., stainless steel, a gold alloy, titanium. The size of the platform depends upon tooth location and/or patient characteristics, among possible other things. For example, a platform for a particular tooth location is shaped so as not to interfere with any adjacent teeth.

As mentioned, the configuration (e.g., size) and shape of a particular post or base may vary. For example, depending upon implant location and patient characteristics, post diameters may be in the general range of from about 1 mm to about 4 mm. However, for most patients, post diameters will be from and including 1.6 mm to and including 2.5 mm. Similarly, depending upon implant location and patient characteristics, post lengths may be in the general range of from about 5 mm to about 16 mm. The length that a post enters the jawbone depends upon implant location, base configuration and patient characteristics.

Exemplary sizes for posts are as follows: post 12b of implant 10b (double post)—8 mm-12 mm in length and 1.6 mm-2.0 mm in diameter; post 12b of implant 10c (triple post)—8 mm-12 mm in length and 1.6 mm-2.0 mm in diameter; post 12c of implant 10c (single post)—10 mm-13 mm in length and 1.6 mm-2.0 mm in diameter. The posts of the embodiments of FIGS. 1, 2 and 10 have similar dimensions.

With respect to the configuration (and size) of the base, For example, depending upon implant location and patient characteristics, a base may be configured to fit within a space of approximately 10 mm×10 mm. However, the base may be longer or wider as discussed above with respect to the jawbone and the implant location, etc. For example, as discussed above, the base corresponds generally to a cross-sectional slice of the tooth formerly at the implant location, and may be configured to be received within the width of the jawbone at the implant location, and the length of the base may corresponds generally to that of a tooth formerly at the implant location, but may be longer. For example, a circular base fitting within a 10 mm×10 mm space may have a diameter of, e.g., 10 mm, or 7 mm, etc., and a triangular base may have a base dimension of 10 mm and a height of 10 mm, or smaller, etc., or other dimensions depending upon the configuration of the triangle, etc. The thickness of the base may be in the general range of 1 mm-4 mm, but is expected to be about 2 mm for most patients. The thickness of the base for the embodiments of FIGS. 11-17 is about 2 mm. The bases of the embodiments of FIGS. 1, 2 and 10 may have similar sizes.

As mentioned discussed above, specific post and base sizes, configurations, etc., may vary.

As a general matter, the sizes of the caps 57a and 57b are proportionate.

In the embodiments described above, the larger surface area provided by the platform and base plate and the loading of thereof against the jawbone provides a stable and permanent fixed base for single and multiple tooth implants. The use of a relatively thin post or posts can minimize the invasiveness of the procedure, both at a single root or multiple root tooth location, which can permit immediate loading of fixed prosthetic devices, enhance patient tolerance to the procedure, and reduce healing time.

Training time for professionals to perform the procedures describe above is expected to be relatively short, e.g., about two weeks.

As for implants in general, it is expected that not all patients will be candidates for the implants that embody the invention. However, for suitable candidates, although patient tolerance and healing with vary with patients, their age, state of health, etc., it is expected that the procedures for installing implants which embody the invention will be more easily tolerated and involve shorter healing periods, e.g., approximately two months.

While the invention has been described and illustrated in connection with preferred embodiments, many variations and modifications as will be evident to those skilled in this art may be made without departing from the spirit and scope of the invention as defined by the claims, and the invention is thus not to be limited to the precise details of methodology or construction set forth above as such variations and modifications are intended to be included within the scope of the invention as defined by the claims.

What is claimed is:

1. A dental implant adapted to be installed in a mouth, comprising:
   three posts each of which includes a screw thread extending along at least a portion thereof, the posts being adapted to be secured to a jawbone with at least a portion of the screw thread in the jawbone, each post having a diameter in the range of about 1 mm to about 4 mm;
   a base comprising opposed sides a first of which is adapted to contact the jawbone and a second of which includes a raised portion, the base including a hole therein at least through the first side thereof for each post;
   a first fastener system comprising structure associated with the posts and the base which engage during tightening of the first fastener system to force and load the base against the jawbone in contact with the jawbone along the first side of the base;
   a single preformed core including a recess in a first end thereof, the core receiving in the recess thereof the raised portion of the base with the first end of the core extending to the second end of the base, the core being sized to at least partially overlay the base and at least partially overlay the holes, the core extending away from the second side of the base and being adapted to be received in a prosthetic device; and a second fastener system which mechanically secures the preformed core to the base, the second fastener system comprising a screw which engages the core and at least the raised portion of the base.

2. A dental implant adapted to be installed in a mouth, comprising:
a plurality of posts each of which includes a screw thread extending along at least a portion thereof, the posts being adapted to be secured to a jawbone with at least a portion of the screw thread in the jawbone, each post having a diameter in the range of about 1 mm to about 4 mm;
a base comprising opposed sides a first of which is adapted to contact the jawbone and a second of which includes a raised portion, the base including a hole therein at least through the first side thereof for each post;
a first fastener system comprising structure associated with the posts and the base which engage during tightening of the first fastener system to force and load the base against the jawbone in contact with the jawbone along the first side of the base;
a single preformed core including a recess in a first end thereof, the core receiving in the recess thereof the raised portion of the base with the first end of the core extending to the second end of the base, the core being sized to at least partially overlay the base and at least partially overlay the holes, the core extending away from the second side of the base and being adapted to be received in a prosthetic device; and
a second fastener system which mechanically secures the preformed core to the base, the second fastener system comprising a screw which engages the core and at least the raised portion of the base.

3. A dental implant adapted to be installed in a mouth, comprising:
three posts each of which includes a screw thread extending along at least a portion thereof, the posts being adapted to be secured to a jawbone with at least a portion of the screw thread in the jawbone, each post having a diameter in the range of about 1.6 mm to about 2.5 mm;
a base comprising opposed sides a first of which is adapted to contact the jawbone and a second of which includes a raised portion, the base including a hole therein at least through the first side thereof for each post;
a first fastener system comprising structure associated with the posts and the base which engage during tightening of the first fastener system to force and load the base against the jawbone in contact with the jawbone along the first side of the base;
a single preformed core including a recess in a first end thereof, the core receiving in the recess thereof the raised portion of the base with the first end of the core extending to the second end of the base, the core being sized to at least partially overlay the base and at least partially overlay the holes, the core extending away from the second side of the base and being adapted to be received in a prosthetic device; and
a second fastener system which mechanically secures the preformed core to the base, the second fastener system comprising a screw which engages the core and at least the raised portion of the base.

4. A dental implant adapted to be installed in a mouth, comprising:
a plurality of posts each of which includes a screw thread extending along at least a portion thereof, the posts being adapted to be secured to a jawbone with at least a portion of the screw thread in the jawbone, each post having a diameter in the range of about 1.6 mm to about 2.5 mm;
a base comprising opposed sides a first of which is adapted to contact the jawbone and a second of which includes a raised portion, the base including a hole therein at least through the first side thereof for each post;
a first fastener system comprising structure associated with the posts and the base which engage during tightening of the first fastener system to force and load the base against the jawbone in contact with the jawbone along the first side of the base;
a single preformed core including a recess in a first end thereof, the core receiving in the recess thereof the raised portion of the base with the first end of the core extending to the second end of the base, the core being sized to at least partially overlay the base and at least partially overlay the holes, the core extending away from the second side of the base and being adapted to be received in a prosthetic device; and
a second fastener system which mechanically secures the preformed core to the base, the second fastener system comprising a screw which engages the core and at least the raised portion of the base.

5. The dental implant of claim 1, 2, 3 or 4, wherein the base comprises a base plate comprising opposed major sides and at least one minor side, the first side and second sides being major sides.

6. The dental implant of claim 1, 2, 3 or 4, wherein the base comprises a base plate comprising opposed major sides and at least one minor side, the first side and second sides being major sides and wherein the opposed major sides of the base plate comprise parallel portions and the at least one minor side is transverse to the parallel portions.

7. The dental implant of claim 1, 2, 3 or 4, wherein the first fastener system engaging structure comprises structure associated with each hole in the base that engages with the structure associated with a respective post, and wherein the first fastener system operates to engage the structure associated with a respective post and a respective hole during securement of the respective post to the jawbone.

8. The dental implant of claim 1, 2, 3 or 4, wherein the dental implant is adapted to be installed at a location in the mouth approximately formerly occupied by a tooth having two or more roots.

9. The combination of a dental implant according to claim 1, 2, 3 or 4 and a prosthetic device adapted to be attached to the core.

10. The combination of claim 9, wherein the prosthetic device comprises structure replacing a single tooth.

11. The combination of claim 9, wherein the prosthetic device comprises structure forming part of a multi-tooth replacement.

12. The combination of claim 9, wherein the prosthetic device comprises a fixed prosthetic device.

13. The combination of claim 9, wherein the prosthetic device comprises a removable prosthetic device.

14. The dental implant of claim 1, 2, 3 or 4, wherein the implant is adapted to replace a tooth and the base has a configuration that is adapted to extend along the jawbone for approximately a distance that the replaced tooth formerly extended along the jawbone.

15. The dental implant of claim 1, 2, 3 or 4, wherein each post includes a shaft portion and wherein the structure associated with each post comprises a head portion which is larger that the respective hole, each post being adapted to be installed with its shaft portion passing through the respective hole and its head portion engaging the base.

16. The dental implant of claim 1, 2, 3 or 4, wherein the core and the base each are configured such that in the installed condition of the implant the core entirely overlays the base.

17. The dental implant of claim 16 comprising a prosthetic device attached to the core, the prosthetic device being configured to entirely overlay the core.

18. The dental implant of claim 1, 2, 3 or 4, wherein the core and the base each are configured such that in the installed condition of the implant the core overlays a first central portion of the base including at least a portion of each hole and does not overlay a second peripheral portion of the base outward of the first central portion of the base.

19. The dental implant of claim 18 comprising a prosthetic device attached to the core, the prosthetic device being configured to entirely overlay the core and to also overlay the second peripheral portion of the base.

20. The dental implant of claim 1, 2, 3 or 4, wherein the second fastener system comprises mutually engaging threaded portions associated with the screw and the base.

21. The dental implant of claim 1, 2, 3 or 4, wherein the screw includes a shaft and a head, the shaft being sized to pass through a hole in the core and the head being larger than at least a portion of the hole in the core, the shaft and at least the raised portion of the base including complementary threaded portions, the threaded portion of the base receiving the threaded portion of the shaft.

* * * * *